(12) United States Patent
Fedie et al.

(10) Patent No.: US 10,239,812 B2
(45) Date of Patent: Mar. 26, 2019

(54) SYSTEMS AND METHODS FOR SYNTHESIS OF PHENOLICS AND KETONES

(71) Applicant: SarTec Corporation, Anoka, MN (US)

(72) Inventors: Ronald Leigh Fedie, Maplewood, MN (US); Bingwen Yan, Shoreview, MN (US); Larry C. McNeff, Anoka, MN (US); Peter G. Greuel, Anoka, MN (US); Clayton V. McNeff, Andover, MN (US)

(73) Assignee: SarTec Corporation, Anoka, MN (US)

( * ) Notice: Subject to any disclaimer, the term of this patent is extended or adjusted under 35 U.S.C. 154(b) by 0 days.

(21) Appl. No.: 15/963,583

(22) Filed: Apr. 26, 2018

(65) Prior Publication Data

US 2018/0312457 A1 Nov. 1, 2018

Related U.S. Application Data

(60) Provisional application No. 62/491,021, filed on Apr. 27, 2017.

(51) Int. Cl.

| | | |
|---|---|---|
| *C07C 27/00* | (2006.01) | |
| *C07C 49/11* | (2006.01) | |
| *C08J 7/00* | (2006.01) | |
| *B01J 19/00* | (2006.01) | |
| *B01J 23/00* | (2006.01) | |
| *C07C 27/26* | (2006.01) | |
| *C08J 7/12* | (2006.01) | |
| *B01J 19/24* | (2006.01) | |
| *B01J 19/32* | (2006.01) | |

(52) U.S. Cl.
CPC .............. *C07C 49/11* (2013.01); *C07C 27/26* (2013.01); *C08J 7/12* (2013.01); *B01J 19/0013* (2013.01); *B01J 19/2415* (2013.01); *B01J 19/32* (2013.01); *B01J 23/002* (2013.01); *B01J 2219/00051* (2013.01); *B01J 2219/00162* (2013.01); *C08J 2301/02* (2013.01)

(58) Field of Classification Search
CPC ... C07C 49/11; C07C 27/26; C08J 7/12; B01J 19/32; B01J 23/002
See application file for complete search history.

(56) References Cited

U.S. PATENT DOCUMENTS

| | | |
|---|---|---|
| 1,873,537 A | 8/1932 | Brown et al. |
| 2,014,408 A | 9/1935 | Woodhouse |
| 2,154,835 A | 4/1939 | Eisenlohr |
| 2,383,632 A | 8/1945 | Trent |
| 2,679,471 A | 5/1954 | Ayers et al. |
| 2,851,468 A | 9/1958 | Snyder |
| 3,383,396 A | 5/1968 | Cahn et al. |
| 4,098,809 A | 7/1978 | Pagani |
| 4,138,336 A | 2/1979 | Mendel et al. |
| 4,216,337 A | 8/1980 | Baba et al. |
| 4,225,630 A | 9/1980 | Pitchon |
| 4,242,455 A | 12/1980 | Muller et al. |
| 4,425,433 A | 1/1984 | Neves |
| 4,487,933 A | 12/1984 | Mixan et al. |
| 4,582,589 A | 4/1986 | Ushizawa et al. |
| 4,716,218 A | 12/1987 | Chen et al. |
| 4,808,526 A | 2/1989 | Lawford |
| 4,861,739 A | 8/1989 | Pellet et al. |
| 4,885,405 A | 12/1989 | Dornhagen et al. |
| 4,891,459 A | 1/1990 | Knight et al. |
| 4,950,812 A | 1/1990 | Jacobs et al. |
| 4,911,941 A | 3/1990 | Katz et al. |
| 5,108,597 A | 4/1992 | Funkenbusch et al. |
| 5,108,897 A | 4/1992 | Steinetz et al. |
| 5,179,219 A | 1/1993 | Priegnitz |
| 5,182,016 A | 1/1993 | Funkenbusch et al. |
| 5,231,017 A | 7/1993 | Lantero et al. |
| 5,252,762 A | 10/1993 | Denton et al. |
| 5,254,262 A | 10/1993 | Funkenbusch et al. |
| 5,271,833 A | 12/1993 | Funkenbusch et al. |
| 5,298,650 A | 3/1994 | Waller et al. |
| 5,308,364 A | 5/1994 | Gutierrez et al. |
| 5,308,365 A | 5/1994 | Kesling et al. |

(Continued)

FOREIGN PATENT DOCUMENTS

| | | |
|---|---|---|
| AU | 2011200090 | 2/2011 |
| BR | 8202429 | 11/1983 |

(Continued)

OTHER PUBLICATIONS

Adebanjo, Adenike O. et al., "Production of Diesel-Like Fuel and Other Value-Added Chemicals from Pyrolysis of Animal Fat," Energy & Fuels, vol. 19, 2005, pp. 1735-1741 (7 pages).

Aimaretti, N. et al., "Batch Study of Glycerol Decomposition in One-Stage Supercritical Production of Biodiesel," Energy & Fuels 2009, vol. 23, pp. 1076-1080 (5 pages).

Akhtar, Javaid et al., "A Review on Process Conditions for Optimum Bio-Oil Yield in Hydrothermal Liquefaction of Biomass," Renewable and Sustainable energy Reviews 15 (2011), pp. 1615-1624 (10 pages).

Albrecht, Ko et al., "A Brief Literature Overview of Various Routes to Biorenewable Fuels from Lipids for the National Alliance for Advanced Biofuels and Bio-products (NAABB) Consortium," U.S. Department of Energy, PNNL-20279, 2011 (16 pages).

(Continued)

*Primary Examiner* — Sikarl A Witherspoon

(74) *Attorney, Agent, or Firm* — Pauly, DeVries Smith & Deffner LLC

(57) ABSTRACT

Embodiments herein relate to apparatus and systems for phenolic and ketone synthesis and methods regarding the same. In an embodiment, a method of producing phenolics and ketones is included. The method can specifically include forming a reaction mixture comprising nanocrystalline cellulose (NCC) and water. The method can also include contacting the reaction mixture with a metal oxide catalyst at a temperature of 350 degrees Celsius or higher and a pressure of at least about 3200 psi to form a reaction product mixture. The reaction product mixture can include at least about 20 wt. % phenolics and at least about 10 wt. % ketones as a percentage of the total mass of nanocrystalline cellulose (NCC). Other embodiments are also included herein.

30 Claims, 6 Drawing Sheets

(56) References Cited

U.S. PATENT DOCUMENTS

| | | |
|---|---|---|
| 5,321,197 A | 6/1994 | Angstadt et al. |
| 5,346,619 A | 9/1994 | Funkenbusch et al. |
| 5,350,879 A | 9/1994 | Engel et al. |
| 5,389,240 A | 2/1995 | Gillespie et al. |
| 5,508,457 A | 4/1996 | Bayense et al. |
| 5,527,970 A | 6/1996 | Hwan et al. |
| 5,532,392 A | 7/1996 | Gheorghiu |
| 5,540,834 A | 7/1996 | Carr et al. |
| 5,651,953 A | 7/1997 | Yokoyama et al. |
| 5,859,270 A | 1/1999 | Kolstad et al. |
| 5,908,946 A | 6/1999 | Stern et al. |
| 5,972,118 A | 10/1999 | Hester et al. |
| 5,985,137 A | 11/1999 | Ohsol et al. |
| 6,090,959 A | 7/2000 | Hirano et al. |
| 6,153,773 A | 11/2000 | Kolstad et al. |
| 6,211,390 B1 | 4/2001 | Peter et al. |
| 6,376,701 B1 | 4/2002 | Chavan et al. |
| 6,392,062 B1 | 5/2002 | Haas |
| 6,407,269 B2 | 6/2002 | Kaita et al. |
| 6,433,146 B1 | 8/2002 | Cheryan |
| 6,441,202 B1 | 8/2002 | Lightner |
| 6,489,496 B2 | 12/2002 | Barnhorst et al. |
| 6,538,146 B2 | 3/2003 | Turck |
| 6,666,074 B2 | 12/2003 | Gerner et al. |
| 6,712,867 B1 | 3/2004 | Boocock |
| 6,713,051 B2 | 3/2004 | Mayes et al. |
| 6,719,815 B2 | 4/2004 | Nanninga et al. |
| 6,768,015 B1 | 7/2004 | Luxem et al. |
| 6,878,837 B2 | 4/2005 | Bournay et al. |
| 6,887,283 B1 | 5/2005 | Ginosar et al. |
| 6,960,672 B2 | 11/2005 | Nakayama et al. |
| 6,963,004 B2 | 11/2005 | Ahtchi-Ali et al. |
| 6,965,044 B1 | 11/2005 | Hammond et al. |
| 6,979,426 B2 | 12/2005 | Teall et al. |
| 6,982,340 B2 | 1/2006 | Mumura et al. |
| 7,045,100 B2 | 5/2006 | Ergun et al. |
| 7,097,770 B2 | 8/2006 | Lysenko |
| 7,101,464 B1 | 9/2006 | Pringle |
| 7,112,688 B1 | 9/2006 | Tysinger et al. |
| 7,126,032 B1 | 10/2006 | Aiken |
| 7,135,308 B1 | 11/2006 | Bush |
| 7,138,536 B2 | 11/2006 | Bournay et al. |
| 7,145,026 B2 | 12/2006 | Fleisher |
| 7,151,187 B2 | 12/2006 | Delfort et al. |
| 7,179,379 B2 | 2/2007 | Appel et al. |
| 7,211,681 B2 | 5/2007 | Furuta |
| 7,288,685 B2 | 10/2007 | Marker |
| 7,301,060 B2 | 11/2007 | Appel et al. |
| 7,309,592 B2 | 12/2007 | Offerman et al. |
| 7,312,355 B2 | 12/2007 | Canos et al. |
| 7,321,052 B2 | 1/2008 | Miller et al. |
| 7,371,308 B1 | 5/2008 | Hackl et al. |
| RE40,419 E | 7/2008 | Norbeck et al. |
| 7,438,785 B2 | 10/2008 | Meier et al. |
| 7,452,841 B2 | 11/2008 | Ignatchenko et al. |
| 7,476,296 B2 | 1/2009 | Appel et al. |
| 7,498,454 B2 | 3/2009 | Redlingshoefer |
| 7,501,379 B2 | 3/2009 | Ignatchenko et al. |
| 7,507,846 B2 | 3/2009 | Pelly |
| 7,514,575 B2 | 4/2009 | Ginosar et al. |
| 7,514,657 B2 | 4/2009 | Moreira et al. |
| 7,563,915 B2 | 7/2009 | Matson |
| 7,582,784 B2 | 9/2009 | Banavali et al. |
| 7,592,470 B2 | 9/2009 | Lacome et al. |
| 7,601,858 B2 | 10/2009 | Cantrell et al. |
| 7,635,398 B2 | 12/2009 | Bertram et al. |
| 7,659,432 B2 | 2/2010 | Ignatchenko et al. |
| 7,666,234 B2 | 2/2010 | Ghosh et al. |
| 7,678,163 B2 | 3/2010 | Iversen et al. |
| 7,683,232 B2 | 3/2010 | Schmidt et al. |
| 7,691,159 B2 | 4/2010 | Li |
| 7,696,376 B2 | 4/2010 | Furuta |
| 7,754,643 B2 | 7/2010 | Srinivas et al. |
| 7,771,699 B2 | 8/2010 | Adams et al. |
| 7,772,414 B1 | 8/2010 | Hybertson et al. |
| 7,777,085 B2 | 8/2010 | Berry et al. |
| 7,780,946 B2 | 8/2010 | Wormsbecher |
| 7,790,651 B2 | 9/2010 | Lin |
| 7,850,841 B2 | 12/2010 | Koivusalmi et al. |
| 7,851,643 B2 | 12/2010 | Hillion et al. |
| 7,857,872 B2 | 12/2010 | Krasutsky et al. |
| 7,880,043 B2 | 2/2011 | Chapus et al. |
| 7,883,882 B2 | 2/2011 | Franklin et al. |
| 7,897,798 B2 | 3/2011 | Mcneff et al. |
| 7,925,273 B2 | 4/2011 | Fomukong et al. |
| 7,928,273 B2 | 4/2011 | Bradin |
| 7,935,515 B2 | 5/2011 | Franklin et al. |
| 7,943,791 B2 | 5/2011 | Mcneff |
| 7,967,973 B2 | 6/2011 | Myllyoja et al. |
| 7,998,339 B2 | 8/2011 | Myllyoja et al. |
| 8,003,833 B2 | 8/2011 | Appel et al. |
| 8,008,516 B2 | 8/2011 | Cantrell et al. |
| 8,017,796 B2 | 9/2011 | Mcneff et al. |
| 8,022,258 B2 | 9/2011 | Myllyoja et al. |
| 8,076,498 B2 | 12/2011 | Elst et al. |
| 8,361,174 B2 | 1/2013 | McNeff et al. |
| 8,445,709 B2 | 5/2013 | Mcneff et al. |
| 8,466,305 B2 | 6/2013 | Mcneff |
| 8,585,976 B2 | 11/2013 | Mcneff et al. |
| 8,686,171 B2 | 4/2014 | Mcneff et al. |
| 8,697,893 B2 | 4/2014 | Mcneff et al. |
| 9,102,877 B2 | 8/2015 | Mcneff et al. |
| 9,382,491 B2 | 7/2016 | Mcneff et al. |
| 9,388,345 B2 | 7/2016 | Mcneff et al. |
| 2001/0042340 A1 | 11/2001 | Tateno et al. |
| 2002/0010359 A1 | 1/2002 | Kaita et al. |
| 2002/0156305 A1 | 10/2002 | Turck |
| 2002/0173682 A1 | 11/2002 | Tullio et al. |
| 2003/0032819 A1 | 2/2003 | Lightner |
| 2003/0143156 A1 | 7/2003 | Wormsbecher |
| 2003/0199049 A1 | 10/2003 | Nguyen et al. |
| 2003/0199149 A1 | 10/2003 | Lee et al. |
| 2003/0229238 A1 | 12/2003 | Fleisher |
| 2004/0074760 A1 | 4/2004 | Portnoff et al. |
| 2004/0087809 A1 | 5/2004 | Nakayama et al. |
| 2004/0094477 A1 | 5/2004 | Lysenko et al. |
| 2004/0188340 A1 | 9/2004 | Appel et al. |
| 2004/0192980 A1 | 9/2004 | Appel et al. |
| 2004/0192981 A1 | 9/2004 | Appel et al. |
| 2005/0006290 A1 | 1/2005 | Patten |
| 2005/0064577 A1 | 3/2005 | Berzin |
| 2005/0080280 A1 | 4/2005 | Yoo |
| 2005/0112739 A1 | 5/2005 | Golubkov |
| 2005/0118409 A1 | 6/2005 | McNeff et al. |
| 2005/0137411 A1 | 6/2005 | Ahtchi-Ali et al. |
| 2005/0204612 A1 | 9/2005 | Connemann et al. |
| 2005/0239182 A1 | 10/2005 | Berzin |
| 2005/0260553 A1 | 11/2005 | Berzin |
| 2005/0261509 A1 | 11/2005 | Delfort et al. |
| 2005/0266139 A1 | 12/2005 | Lacome et al. |
| 2005/0274065 A1 | 12/2005 | Portnoff et al. |
| 2006/0004237 A1 | 1/2006 | Appel et al. |
| 2006/0014974 A1 | 1/2006 | Bournay et al. |
| 2006/0041152 A1 | 2/2006 | Cantrell et al. |
| 2006/0041153 A1 | 2/2006 | Cantrell et al. |
| 2006/0043003 A1 | 3/2006 | Moreira et al. |
| 2006/0080891 A1 | 4/2006 | Ghosh et al. |
| 2006/0135823 A1 | 6/2006 | Jun et al. |
| 2006/0149087 A1 | 7/2006 | Furuta |
| 2006/0224005 A1 | 10/2006 | Felly |
| 2006/0246141 A1 | 11/2006 | Liversidge et al. |
| 2006/0252950 A1 | 11/2006 | Ginosar et al. |
| 2006/0260186 A1 | 11/2006 | Iversen et al. |
| 2006/0288636 A1 | 12/2006 | Iijima et al. |
| 2007/0010682 A1 | 1/2007 | Myllyoja et al. |
| 2007/0027338 A1 | 2/2007 | Furuta |
| 2007/0037994 A1 | 2/2007 | Canos et al. |
| 2007/0066838 A1 | 3/2007 | Hillion et al. |
| 2007/0089356 A1 | 4/2007 | Krasutsky et al. |
| 2007/0093380 A1 | 4/2007 | Srinivas et al. |
| 2007/0098625 A1 | 5/2007 | Adams et al. |
| 2007/0137097 A1 | 6/2007 | Ikura |
| 2007/0196892 A1 | 8/2007 | Winsness et al. |
| 2007/0225383 A1 | 9/2007 | Cortright et al. |

(56) References Cited

U.S. PATENT DOCUMENTS

| | | |
|---|---|---|
| 2007/0238905 A1 | 10/2007 | Arredondo et al. |
| 2007/0282118 A1 | 12/2007 | Gupta et al. |
| 2007/0283619 A1 | 12/2007 | Hillion et al. |
| 2008/0051592 A1 | 2/2008 | Mcneff et al. |
| 2008/0161615 A1 | 7/2008 | Chapus |
| 2008/0188676 A1 | 8/2008 | Anderson et al. |
| 2008/0194811 A1 | 8/2008 | Mcneff |
| 2008/0197052 A1 | 8/2008 | Mcneff et al. |
| 2008/0275144 A1 | 11/2008 | Van Hardeveld et al. |
| 2008/0318763 A1 | 12/2008 | Anderson |
| 2008/0319236 A1 | 12/2008 | Mcneff et al. |
| 2009/0014354 A1 | 1/2009 | Knuuttila et al. |
| 2009/0029445 A1 | 1/2009 | Eckelberry et al. |
| 2009/0069586 A1 | 3/2009 | Oku et al. |
| 2009/0126262 A1 | 5/2009 | Asthana et al. |
| 2009/0227823 A1 | 9/2009 | Huber et al. |
| 2009/0255171 A1 | 10/2009 | Dumesic et al. |
| 2009/0281056 A1 | 11/2009 | Mori et al. |
| 2009/0297495 A1 | 12/2009 | Kerovuo et al. |
| 2010/0010246 A1 | 1/2010 | Yan et al. |
| 2010/0048930 A1 | 2/2010 | Elst et al. |
| 2010/0050502 A1 | 3/2010 | Wu et al. |
| 2010/0081181 A1 | 4/2010 | Berry et al. |
| 2010/0081835 A1 | 4/2010 | Wu et al. |
| 2010/0087670 A1 | 4/2010 | Wang et al. |
| 2010/0113849 A1 | 5/2010 | Bartek et al. |
| 2010/0147771 A1 | 6/2010 | Mcneff et al. |
| 2010/0151535 A1 | 6/2010 | Franklin et al. |
| 2010/0151539 A1 | 6/2010 | Franklin et al. |
| 2010/0170143 A1 | 7/2010 | Mcneff et al. |
| 2010/0170147 A1 | 7/2010 | Mcneff et al. |
| 2010/0191004 A1 | 7/2010 | Mcneff et al. |
| 2010/0287823 A1 | 11/2010 | Misra et al. |
| 2010/0305346 A1 | 12/2010 | Hara et al. |
| 2010/0324310 A1 | 12/2010 | Dumesic et al. |
| 2011/0009501 A1 | 1/2011 | Ernst |
| 2011/0035993 A1 | 2/2011 | Loescher |
| 2011/0060153 A1 | 3/2011 | Mcneff et al. |
| 2011/0105814 A1 | 5/2011 | Koivusalmi et al. |
| 2011/0172450 A1 | 7/2011 | Mcneff et al. |
| 2011/0184201 A1 | 7/2011 | Mcneff |
| 2011/0213040 A1 | 9/2011 | Hassan et al. |
| 2011/0287991 A1 | 11/2011 | Dubois |
| 2011/0306808 A1 | 12/2011 | Appel et al. |
| 2011/0319849 A1 | 12/2011 | Collias et al. |
| 2012/0055077 A1 | 3/2012 | Savage et al. |
| 2013/0345457 A1 | 12/2013 | Mcneff |
| 2014/0046104 A1 | 2/2014 | Mcneff et al. |
| 2014/0115955 A1 | 5/2014 | Mcneff et al. |
| 2017/0029711 A1 | 2/2017 | Mcneff et al. |

FOREIGN PATENT DOCUMENTS

| | | |
|---|---|---|
| BR | 06001602 | 10/2007 |
| CA | 2601472 | 9/2006 |
| CA | 2607931 | 11/2006 |
| CA | 2660049 | 9/2015 |
| CN | 1680514 | 10/2005 |
| CN | 1718679 | 1/2006 |
| CN | 1858160 | 11/2006 |
| CN | 1887417 | 1/2007 |
| CN | 1928016 | 3/2007 |
| CN | 101870989 | 10/2010 |
| DE | 19620378 | 2/1999 |
| DE | 102004056786 | 7/2005 |
| DE | 102005038137 | 2/2007 |
| EP | 0169953 | 2/1986 |
| EP | 0198243 | 10/1986 |
| EP | 0506428 A1 | 9/1992 |
| EP | 0535290 | 4/1993 |
| EP | 1396483 | 3/2004 |
| EP | 1505048 | 2/2005 |
| EP | 1580255 | 9/2005 |
| EP | 1607467 | 12/2005 |
| EP | 1642560 | 4/2006 |
| EP | 1681281 | 7/2006 |
| EP | 1869173 | 12/2007 |
| EP | 0507217 A1 | 10/2010 |
| EP | 2290035 | 3/2011 |
| EP | 2290045 | 3/2011 |
| FR | 2188612 | 1/1974 |
| FR | 2679471 | 1/1993 |
| FR | 2890656 | 3/2007 |
| FR | 2938536 | 5/2010 |
| FR | 2947564 | 1/2011 |
| GB | 2132222 | 7/1984 |
| JP | 02289692 | 11/1990 |
| JP | 6313188 | 11/1994 |
| JP | 11228494 | 8/1999 |
| JP | 2000355692 | 12/2000 |
| JP | 2005126346 | 5/2005 |
| JP | 2005177722 | 7/2005 |
| JP | 2006129735 | 5/2006 |
| JP | 2007153943 | 6/2007 |
| JP | 2007153944 | 6/2007 |
| JP | 2007190450 | 8/2007 |
| JP | 2008111085 | 5/2008 |
| WO | 9108677 | 6/1991 |
| WO | 1996027632 | 9/1996 |
| WO | 9707187 | 2/1997 |
| WO | 9950213 | 10/1999 |
| WO | 2000005327 | 2/2000 |
| WO | 02102337 | 12/2002 |
| WO | 03062358 | 7/2003 |
| WO | 03087279 | 10/2003 |
| WO | 03094598 | 11/2003 |
| WO | 2004085585 | 10/2004 |
| WO | 2004096962 | 11/2004 |
| WO | 2004108873 | 12/2004 |
| WO | 2005000782 | 1/2005 |
| WO | 2005021697 | 3/2005 |
| WO | 2008029132 | 3/2005 |
| WO | 2005035479 | 4/2005 |
| WO | 2005093015 | 10/2005 |
| WO | 2005123890 | 12/2005 |
| WO | 2006041253 | 4/2006 |
| WO | 2006070661 | 7/2006 |
| WO | 2006081644 | 8/2006 |
| WO | 2006088254 | 8/2006 |
| WO | 2006093896 | 9/2006 |
| WO | 2006094986 | 9/2006 |
| WO | 2006096834 | 9/2006 |
| WO | 2006121584 | 11/2006 |
| WO | 2007011343 | 1/2007 |
| WO | 2007012190 | 2/2007 |
| WO | 2007025360 | 3/2007 |
| WO | 2007029851 | 3/2007 |
| WO | 2007038605 | 4/2007 |
| WO | 2007043062 | 4/2007 |
| WO | 2007068097 | 6/2007 |
| WO | 2007072972 | 6/2007 |
| WO | 2007077950 | 7/2007 |
| WO | 2007111604 | 10/2007 |
| WO | 2007140395 | 12/2007 |
| WO | 2007141293 | 12/2007 |
| WO | 2007142983 | 12/2007 |
| WO | 2007146636 | 12/2007 |
| WO | 2008012275 | 1/2008 |
| WO | 2008019325 | 2/2008 |
| WO | 2008034109 | 3/2008 |
| WO | 2008041038 | 4/2008 |
| WO | 2008101007 | 8/2008 |
| WO | 2008101032 | 8/2008 |
| WO | 2008152199 | 12/2008 |
| WO | 2009002880 | 12/2008 |
| WO | 2009003039 | 12/2008 |
| WO | 2009007234 | 1/2009 |
| WO | 2009115322 | 9/2009 |
| WO | 2009143159 | 11/2009 |
| WO | 2010005391 | 1/2010 |
| WO | 2010036333 | 4/2010 |
| WO | 2010075437 | 7/2010 |
| WO | 2010132628 | 11/2010 |
| WO | 2010141794 | 12/2010 |

(56) References Cited

FOREIGN PATENT DOCUMENTS

| WO | 2010144597 | 12/2010 |
|---|---|---|
| WO | 2010147955 | 12/2010 |
| WO | 2010148057 | 12/2010 |
| WO | 2011004111 | 1/2011 |
| WO | 2011012438 | 2/2011 |
| WO | 2011012439 | 2/2011 |
| WO | 2011012440 | 2/2011 |
| WO | 2011130573 | 10/2011 |
| WO | 2011150410 | 12/2011 |
| WO | 2011150411 | 12/2011 |
| WO | 2014008355 | 1/2014 |

OTHER PUBLICATIONS

Alonso, David M. et al., "Catalytic Conversion of Biomass to Biofuels," Green Chem., vol. 12, 2010, pp. 1493-1513 (21 pages).
Alonso, David M. et al., "Production of Liquid Hydrocarbon Transportation Fuels by Oligomerization of Biomass-Derived C9 Alkenes," Green Chem., vol. 12, 2010, pp. 992-999 (8 pages).
An, Lu et al., "The Influence of Ni Loading Coke Formation in Steam Reforming of Acetic Acid," Renewable Energy, vol. 36, 2011, pp. 930-935 (6 pages).
Annen, M J. et al., "Development of Porous Zirconia spheres by Polymerization-Induced Colloid Aggregation—Effect of Polymerization Rate," Journal of Materials Science, vol. 29, 1994, pp. 6123-6130 (8 pages).
Anon, "Beatrice Biodiesel Selects Axens Exterfip-H Technology," Biodiesel Magazine Jun. 2006, Unknown (2 pages).
Barteau, Mark A. "Organic Reactions at Well-Defined Oxide Surfaces," Chem. Rev., vol. 96, 1996, pp. 1413-1430 (18 pages).
Bcc Research, "Global Market for Catalyst Regeneration," MarketResearch.com http://www.marketresearch.com/product/display.asp?productid=1354464 2006, 1-20 (20 pages).
Bicker, et al., Green Chemistry 2003, 5. 2005, 280-284 (5 pages).
Billaud, F. et al., "Catalytic Cracking of Octanoic Acid," Journal of Analytical and Applied Pyrolysis, vol. 58-59, 2001, pp. 605-616 (12 pages).
Billaud, Francis et al., "Pyrolysis of Secondary Raw Material from Used Frying Oils," Récents Progrès en Génie des Procédés, Numéro 94—2007 ISBN 2-910239-68-3, Ed. SFGP, Paris, France (8 pages).
Blackwell, J. A. et al., "A Chromatographic Study of the Lewis Acid-Base Chemistry of Zirconia Surfaces," J. Liquid Chromatog. 1991, 14: 2875-2889 (14 pages).
Blackwell, J. A. et al., "Study of the Fluoride Adsorption Characterisitics of Porous Microparticulate Zirconium Oxide," J. Chromatog. 1991, 549: 43-57 (16 pages).
Bournay, L. et al., "New Heterogeneous Process for Biodiesel Production: A Way to Improve the Quality and the Value of the Crude Glycerin Produced by Biodiesel Plants," Catalysis Today 2005, 106: 190-192 (3 pages).
Brown, Adrian S. et al., "Sulfated Metal Oxide Catalysts: Superactivity through Superacidity?," Green Chemistry Feb. 1999, 17-20 (4 pages).
Bryan, Tom "Adsorbing It All," Biodiesel Magazine Mar. 2005, 40-43 (4 pages).
Busca, Guido "Bases and Basic Materials in Industrial and Environmental Chemistry: A Review of Commerical Processes," Ind. Eng. Chem. Res., vol. 48, 2009, pp. 6486-6511 (26 pages).
Cao, W. et al., "Preparation of Biodiesel from Soybean Oil Using Supercritical Methanol and Co-Solvent," Fuel 2005, 84: 347-351 (5 pages).
Catallo, W. J. et al., "Transformation of Glucose to Volatile and Semi-Volatile Products in Hydrothermal (HT) Systems," Biomass and Bioenergy, vol. 34, 2010, pp. 1-13 (13 pages).
Chen, Ching-Hung et al., "Biodiesel Production from Supercritial Carbon Dioxide Extracted Jatropha Oil Using Subcritical Hydrolysis and Supercritical Methylation," J. of Supercritical Fluids, vol. 52, 2010, pp. 228-234 (7 pages).

Chen, Ching-Hung et al., "Subcritical Hydrolysis and Supercritical Methylation of Supercritical Carbon Dioxide Extraction of Jatropha Oil," Separation and Purification Technology, vol. 74, 2010, pp. 7-13 (7 pages).
Cheng, F W. "China Produces Fuels from Vegetable Oils," Chem. Metall. Eng. Jan. 1945, 99 (1 page).
Chheda, et al., Catalysis Today 2007 123. 2007, 59-70 (12 pages).
Choudhary, T. V. et al., "Renewable Fuels via Catalytic Hydrodeoxygenation," Applied Catalysis A: General, vol. 397, 2011 pp. 1-12 (12 pages).
Collins, K. "Statement of Keith Collins, Chief Economist, U.S. Department of Agriculture before the U.S. Senate Committee on Appropriations, Subcommittee on Agriculture, Rural Development, and Related Agencies: Economic Issues Related to Biofuels.," Unknown www.usda.gov/documents/Farmbill07energy.doc. Aug. 26, 2006, 1-8 (web) (13 pages).
Cottier, et al., Heterocyclic Chemistry 1991, 2. 1991, 233-248 (16 pages).
Czernik, Stefan et al., "Hydrogen by Catalytic Steam Reforming of Liquid Byproducts from biomass Thermoconversion Processes," Ind. Eng. Chem. Res. vol. 41, 2002, pp. 4209-4215 (7 pages).
Dagle, Robert A. et al., "Methanol Steam Reforming for Hydrogen Production," Chem. Rev., vol. 107, 2007, pp. 3992-4021 (30 pages).
Dandik, Levent et al., "Catalytic Conversion of Used Oil to Hydrocarbon Fuels in a Fractionating Pyrolysis Reactor," Energy and Fuels, vol. 12, 1998, pp. 1148-1152 (5 pages).
Danuthai, Tanate et al., "Conversion of Methylesters to Hydrocarbons over an H-ZSM5 Zeolite Catalyst," Applied Catalyst A: General. vol. 361, 2009, pp. 99-105 (7 pages).
De La Casa, R.M. et al., "Modification of the Activities of Two Different lipases from Candida Rugosa with Dextrans," Enzyme and Microbial Technology, vol. 30, 2002, pp. 30-40 (11 pages).
De Lasa, Hugo et al., "Catalytic Steam Gasificationof Biomass: Catalysts, Thermodynamics and Kinetics," Chemical Reviews, vol. 111, 2011, pp. 5404-5433 (30 pages).
De Paula, Ariela V. et al., "Screening of Food Grade Lipases to be Used in Esterification and Intersterification Reactions of Industrial Interest," Appl Biochem Biotechnol, vol. 160, pp. 1146-1156 (11 pages), 2010.
Dean, Morgan et al., "Nanocrystalline Metal Oxide-Based Catalysts for Biodiesel Production from Soybean Oil," #96—Student Poster Session: Catalysis & Reaction Engineering (04016) http://aiche.confex.com/aiche/2006/techprogram/P78366.HTM Nov. 13, 2006, 1 (web) (1 page).
Demirbas, Ayhan "Biodiesel fuels from vegetable oils via catalytic and non-catalytic supercritical alcohol transesterifications and other methods: a survey," Energy Conversion & Management 2003, issue 44 pp. 2093-2109 (17 pages).
Deng, Li et al., "Upgraded Acidic Components of Bio-Oil through Catalytic Ketonic Condensation," Energy & Fuels, vol. 23, 2009, pp. 564-568 (5 pages).
Di Serio, et al., "Synthesis of Biodiesel via Homogeneous Lewis Acid Catalyst," J. Molec. Catal. A Chem. 2005, 239: 111-115 (5 pages).
Di Serio, M. et al., "Transesterification of Soybean Oil to Biodiesel by Using Heterogeneous Basic Catalysts," Ind. Eng. Chem. Res. 2006, 45: 3009-3014 (6 pages).
Dias, et al., Journal of Catalysis, 2005, 229 2005, 414-423 (10 pages).
Dierker, Markus et al., "Surfactants from Oleic, Erucic, and Petroselinic Acid: Synthesis and Properties," Eur. J. Lipid Sci. Technol., vol. 112, 2010, pp. 122-136 (15 pages).
DME Project at Air Products, "Liquid Phase Dimethyl Ether Demonstration in the LaPorte Alternative Fuels Development Unit," Air Products and Chemicals, Inc., Allentown, Pennsylvania (Jan. 2001) (177 pages).
Dorsa, Renato et al., "Basics of Alkali Refining of Vegetable Oils," GEA Westfalia Separator Food Tec GmbH Unknown, 1-28 (28 pages).
Dry, Mark E. "The Fischer-Tropsch process—Commercial Aspects," Catalysis today 6 (3), 1990, pp. 183-206 (24 pages).

(56) References Cited

OTHER PUBLICATIONS

Dry, Mark E. et al., "High Quality Diesel via the Fischer-Tropsch Process—A Review," J. Chem Technol Biotechnol., vol. 77, 2001, pp. 43-50 (8 pages).
Dunlap, C. J. et al., "Zirconia Stationary Phases for Extreme Separations," Anal. Chem. 2001, 73: 598A-607A (11 pages).
Elliott, Brian "Low-cost Biodiesel Production Process Using Waste Oils and Fats," U.S. EPA SBIR Phase I Kick-Off Meeting www.iastate.edu/Inside/2003/0613/biorenewable.jpg Apr. 5, 2007, (1 page).
Fabbri, D. et al., "Dimethyl carbonate as a novel methylating reagent for fatty acids in analytical pyrolysis," Journal of Chromatography, Elsevier Science Publishers B.V, NL LNKDDOI:10.1016/J.CHROMA. 2004.12.077 Feb. 18, 2005 (8 pages).
File History for EP Patent Application No. 07840692.3 downloaded Jun. 19, 2018 (375 pages).
File History for U.S. Appl. No. 12/987,751 downloaded May 31, 2018 (429 pages).
File History for U.S. Appl. No. 11/833,839 downloaded May 31, 2018 (360 pages).
File History for EP Patent Application No. 08729792.5 downloaded Jun. 19, 2018 (262 pages).
File History for U.S. Appl. No. 12/030,801 downloaded May 31, 2018 (325 pages).
File History for EP Patent Application No. 08771929.0 downloaded Jun. 19, 2018 (137 pages).
File History for U.S. Appl. No. 12/146,175 downloaded May 31, 2018 (259 pages).
File History for U.S. Appl. No. 13/080,507 downloaded May 31, 2018 (264 pages).
File History for U.S. Appl. No. 13/909,885 downloaded May 31, 2018 (147 pages).
File History for U.S. Appl. No. 12/540,568 downloaded May 31, 2018 (257 pages).
File History for EP Patent Application No. 10724652.2 downloaded Jun. 19, 2018 (205 pages).
File History for U.S. Appl. No. 12/797,393 downloaded May 31, 2018 (237 pages).
File History for EP Application No. 08729762.8 downloaded Jun. 19, 2018 (216 pages).
File History for U.S. Appl. No. 12/030,649 downloaded May 31, 2018 (252 pages).
File History for U.S. Appl. No. 12/238,750 downloaded May 31, 2018 (202 pages).
File History for U.S. Appl. No. 12/575,198 downloaded May 31, 2018 (296 pages).
File History for U.S. Appl. No. 12/645,119 downloaded May 31, 2018 (316 pages).
File History for U.S. Appl. No. 12/617,125 downloaded May 31, 2018 (375 pages).
File History for U.S. Appl. No. 15/189,428 downloaded May 31, 2018 (270 pages).
File History for U.S. Appl. No. 14/146,601 downloaded May 31, 2018 (359 pages).
File History for U.S. Appl. No. 13/934,713 downloaded May 31, 2018 (1062 pages).
Frykman, Hans B. et al., "Screening Catalytic Lipase Activities with an Analytical Supercritical Fluid Extractor," JAOCS, vol. 75, 1998, pp. 517-520 (4 pages).
Fu, Jie et al., "Activated Carbons for Hydrothermal Decarboxylation of Fatty Acids," ACS Catalysis, vol. 1, 2011, pp. 227-231 (5 pages).
Fu, Jie et al., "Catalytic Hydrothermal Deoxygenation of Palmitic Acid," Energy Environ. Sci., vol. 3, 2010, pp. 311-317 (2 pages).
Fujita, Kazunori et al., "Hydrolysis of Glycerol Trioleate and Extraction of Its Fatty acid Under Co2 Supercritical Conditions," The Chemical Society of Japan, vol. 1, 1995, pp. 79-82 (4 pages).
Fureby, Anna M. et al., "Preparation of Diglycerides by Lipase-Catalyzed Alcoholysis of Triglycerides," Enzyme and Microbial Technology, vol. 20, 1997, pp. 198-206 (9 pages).
Furuta, S. et al., "Biodiesel Fuel Production with Solid Superacid Catalysis is Fixed Bed Reactor Under Atmospheric Pressure," Catalysis Communications 2004, 5: 721-723 (3 pages).
Gaertner, C. A. et al., "Catalytic Coupling of Carboxylic Acids by Ketonization as a Processing Step in Biomass Conversion," Journal of Catalysis, vol. 266, 2009, pp. 71-78 (8 pages).
Gaertner, Christian A. et al., "Catalytic Upgrading of Bio-Oils by Ketonization," ChemSusChem, vol. 2, 2009, pp. 1121-1124 (4 pages).
Gaertner, Christian A. et al., "Ketonization Reactions of Carboxylic Acids and Esters over Ceria-Zirconia as Biomass-Upgrading Processes," Ind. Eng. Chem. Res, vol. 49, 2010, pp. 6027-6033 (7 pages).
Gercel, H. F. et al., "Hydropyrolysis of Extracted Euphorbia rigida in a Well-Swept Fixed-Bed Tubular Reactor," Energy Sources 2002, 24: 423-430 (8 pages).
Glinski, M. et al., "Catalytic Ketonization over Oxide Catalysts X. Transformations of Various Alkyl Heptanoates," Applied Catalysis A: General, vol. 281, 2005, pp. 107-113 (9 pages).
Glinski, M. et al., "Ketones from Monocarboxylic acids: Catalytic Ketonization over Oxide Systems," Applied Catalysis A: General, vol. 128, 1995, pp. 209-217 (7 pages).
Goering, C. E. et al., "Fuel Properties of Eleven Vegetable Oils," Trans ASAE 1982, 25: 1472-1477 (7 pages).
Goodwin, J. G. "Research Activities: Biodiesel Synthesis," Chemical and Biomolecular Engineering at Clemson University http://www.ces.clemson.edu/chemeng/facultypages/goodwin/research.html 2006, 1-5 (5 pages).
Guerbuez, Elif I. et al., "Dual-Bed Catalyst System for C-C Coupling of Biomass-Derived Oxygenated Hydrocarbons to Fuel-Grade Compounds," Green Chemistry, vol. 12, 2010, pp. 223-227 (5 pages).
Guthalugu, Nagesha K. et al., "Optimization of Enzymatic Hydrolysis of Triglycerides in Soy Deodorized Distillate with Supercritical Carbon Dioxide," Biochemical Engineering Journal, vol. 29, 2006, pp. 220-226 (7 pages).
Haas, M. J. et al., "Engine Performance of Biodiesel Fuel Prepared from Soybean Soapstack: A High Quality Renewable Fuel Produced from a Waste Feedstock," Energy Fuels 2001, 15: 1207-1212 (6 pages).
Haas, M. J. et al., "Improving the Economics of Biodiesel Production Through the Use of Low Value Lipids as Feedstocks: Vegetable Oil soapstock," Fuel Process. Technol. 2005, 86: 1087-1096 (10 pages).
Hampson, J.W. et al., "Effect of Moisture Content on Immobilized Lipase-Catalyzed Tricylglycerol Hydrolysis Under Supecritical Carbon Dioxide Flow in a Tubular Fixed-Bed Reactor," JAOCS, vol. 76, 1999, pp. 777-781 (5 pages).
Hampson, J.W. et al., "Separation of Tripalmitin from Its Hydrolysis Products by Simple Isocratic Reversed-Phase High-Performance Liquid Chromatography," JAOCS, vol. 75, 1998, pp. 539-540 (2 pages).
Hara, Michikazu "Biomass conversion by a solid acid catalyst," Energy Environ. Sci., vol. 3, 2010, pp. 601-607 (7 pages).
Harvey, A. P. et al., "Process Intensification of Biodiesel Production Using a Continuous Oscillatory Flow Reactor," J. Chem. Technol. Biotechnol. 2003, 78: 338-341 (4 pages).
Haryanto, Agus et al., "Current Status of Hydrogen Production Techniques by Steam Reforming of Ethanol: A Review," Energy and Fuels, vol. 19, 2005, pp. 2098-2106 (9 pages).
He, Chen et al., "Biodiesel from Transesterification of Cotton Seed Oil by Solid Bases Catalysis," Journal of Chemical Engineering of Chinese Universities Aug. 2006, No. 4 vol. 20 (5 pages).
He, Chen et al., "Biodiesel Production by the transesterification of cottonseed oil by solid acid catalysts," Abstract only, Frontiers of Chemical Engineering in China Feb. 2006, vol. 1, No. 1, pp. 1673-7369 (2 pages).
Henry, R. A. et al., "A Novel Chemical Route to Stable, Regenerable Zirconia-Based Chiral Stationary Phases for HPLC," American Laboratory (News Edition) 2005, 37: 22-24 (2 pages).

(56) References Cited

OTHER PUBLICATIONS

Heyerdahl, Petter H. et al., "Hydrothermal Treatment and Microwave Assisted Pyrolysis of Biomass for Bio-fuel Production-Progress Report," Presentation at UMB and UMN 2006, pp. 1-45 (45 pages).
Hill, J. et al., "Environmental, Economic, and Energetic Costs and Benefits of Biodiesel and Ethanol Biofuels," PNAS 2006, 103(30): 11206-11210 (5 pages).
Hirata, Hirofumi et al., "Enzyme Reaction in Organic Solvent. III. Effect of Water Content and Inhibition of Alcohol for the Catalyzed Transesterification in Tributyrin 1-Octanol," Natl. Chem. Lab. Ind., vol. 38, 1989, pp. 48-52 (5 pages).
Hirata, Hirofumi et al., "Substrate-Solvent Dependence of Enantioselectivity in Porcine Pancreatic Lipase Catalyzed Transesterification Between Tributyrylglycerol and Secondary Alcohol in Organic Solvent," J. Oleo Sci., vol. 51, 2002, pp. 539-547 (9 pages).
Holliday, Russell L. et al., "Hydrolysis of Vegetable Oils in Sub- and Supercritical Water," Industrial and Engineering Chemistry Research, vol. 36, Number, 3, 1997, pp. 932-935 (5 pages).
Idem, Raphael O. et al., "Thermal Cracking of Canola Oil: Reaction Products in the Presence and Absence of Steam," Energy & Fuels . vol. 10, 1995, pp. 1150-11662 (13 pages).
Ignatchenko, Alexey et al., "Interaction of Water with Titania and Zirconia Surfaces," Journal of Molecular Catalysis A: Chemical, vol. 256, 2006, pp. 57-74 (18 pages).
Ignatchenko, Alexey V. "Density Functional Theory Study of Carboxylic Acids Adsorption and Enolization on Monoclinic Zirconia Surfaces," J. Phys. Chem. C., vol. 116, pp. 16012-16018 (7 pages), 2011.
Iijima, Wataru et al., "The Non-glycerol Process of Biodiesel Fuel Treated in Supercritical Methanol (Abstract)," Paper No. 046073, 2004 ASAE Annual Meeting 2004, (1 page).
Iijima, Wataru et al., "Winterized" Bio-Diesel Fuel Produced from Animal Fat, Agro-Energy Laboratory, Dept. of Farm Mechanization and Engineering,National Agricultural ResearchCentre, National Agricultural Research Organization, Japan Unknown (2 pages), 2004.
Immer, Jeremy G. et al., "Catalytic Reaction Pathways in Liquid-Phase Deoxygenation of C18 Free Fatty Acids," Applied Catalysis A: General, vol. 375, 2010, pp. 134-139 (6 pages).
"International Preliminary Report on Patentability," for PCT Application No. PCT/US2013/049250, dated Jan. 15, 2015 (8 pages).
"International Search Report and Written Opinion" for PCT Application No. PCT/US2008/053883, dated Jul. 9, 2008 (9 pages).
"International Search Report and Written Opinion," for PCT/US2013/049250, dated Nov. 1, 2013 (11 pages).
Irimescu, Roxana et al., "Comparison of Acyl Donors for Lipase-Catalyzed Production of 1,3-Dicapryloyl-2-eicosapentaenoylglycerol," JAOCS, vol. 78, 2001, pp. 65-70 (6 pages).
Isayama, Yohei et al., "Biodiesel production by supercritical process with crude bio-methanol prepared by wood gasification," Bioresource Technology, vol. 99, 2008, pp. 4775-4779 (5 pages).
Ishai, Paul B. et al., "Influence of Cyclosporine A on Molecular Interactions in Lyotropic Reverse Hexagonal Liquid Crystals," J. Phys. Chem. B, vol. 114, 2010, pp. 12785-12791 (7 pages).
Ishihara, K. et al., "Direct Ester Condensation from a 1:1 Mixture of Carboxylic Acids and Alcohols Catalyzed by Hafnium (IV) or Zirconium (IV) Salts.," Tetrahedron 2002, 58: 8179-8188 (10 pages).
Isono, Yasuyuki et al., "Interesterification of Triglyceride and Fatty Acid in a Mircoaqueous Reaction System Using Lipase-Surfactant Complex," Biosci. Biotech. Biochem., vol. 59 (9), 1995, 1632-1635 (4 pages).
Jiang, Xiaoxiang et al., "Upgrading Bio-Oil Through Emulsification with Biodiesel: Thermal Stability," Energy Fuels, vol. 24, 2010, pp. 2699-2706 (8 pages).

Jimenez-Morales, I. et al., "Calcined zirconium sulfate supported on MCM-41 silica as acid catalyst for ethanolysis of sunflower oil," Applied Catalysis B: Environmental, vol. 103, 2011, pp. 91-98 (8 pages).
Kahn, A. "Research into Biodiesel Catalyst Screening and Development," Thesis, University of Queensland Brisbane 2002, 1-41 (41 pages).
Kamimura, Yoichiro et al., "Synthesis of 3-Pentanone from 1-Propanol Over Ce02-Fe2O3 Catalysts," Applied catalysis A: General, vol. 252, (2003), pp. 399-410 (12 pages).
Katsivela, E. et al., "Hydrolysis and Ester-Synthesis Activties of Crude Enzyme Preparation," Enzyme and Microbial technology, vol. 17, 1995, pp. 739-745 (7 pages).
Kim, K.S. et al., "Pathways for Carboxylic Acid Decomposition of TiO2," Langmuir, vol. 4, 1988, pp. 945-953 (9 pages).
King, Jerry W. et al., "Hydrolysis of soybean oil in a subcritical water flow reactor," Green Chemistry, vol. 1, 1999, pp. 261-264 (4 pages).
Kiss, Anton A. et al., "Solid Acid Catalysts for Biodiesel Production—Towards Sustainable Energy," Adv. Synth. Catal. 2006, 348: 75-81 (7 pages).
Kittelson, "Biofuels for Engines," Third Annual IREE Research Symposium University of Minnesota, Twin Cities Campus (Nov. 28, 2006) (29 pages).
Knothe, G. "Analytical Methods Used in the Production and Fuel Quality Assessment of Biodiesel," Transactions of the ASAE 2001, 44(2): 193-200 (8 pages), 1997.
Knothe, Gerhard et al., "Bidiesel: The Use of Vegetable Oils and Their Derivatives as Alternative Diesel Fuels," Oil Chemical Research, National Center for Agricultural Utilization Research, Agricultural Research Service, U.S. Department of Agriculture, Peoria, IL 61604 Unknown, 1-36 (36 pages).
Koh, Ashley D. "Non-Catalytic Biodiesel Production from Soybean Oil Using Supercritical Methanol," The 2006 Annual Meeting San Francisco, CA http://aiche.confex.com/aiche/2006/techprogram/P69978.HTM presented Nov. 15, 2006, (1 page).
Kocsisova, Teodora et al., "Hydrolysis of fatty acid in esters in subcritical water," Eur. J. Lipid Sci. Technol., vol. 108, 2006, pp. 652-658 (7 pages).
Kubatova, Alena et al., "Triacylglyceride Thermal Cracking: Pathways to Cyclic Hydrocarbons," Energy & Fuels, 2011 (14 pages).
Kubicka, David et al., "Deactivation of HDS Catalysts in Deoxygenation of Vegetable Oils," Applied Catalysis A: General, vol. 394, 2011, pp. 9-17 (9 pages).
Kubicka, David et al., "Deoxygenation of Vegetable Oils over Sulfided Ni, Mo, and NiMo Catalysts," Applied Catalysis A: General, vol. 372, 2010, pp. 199-208 (10 pages).
Kulkarni, M. et al., "Waste Cooking Oil: An Economical Source for Biodiesel," Ind. Eng. Chem. Res. 2006, 45: 2901-2913 (13 pages).
Kulkarni, Mangesh G. et al., "Solid Acid Catalyxed Biodiesel Production by Simultaneous Esterification and Transesterification," Green Chem. 2006, 8: 1056-1062 (2 pages).
Kusdiana, Dadan et al., "Effects of water on biodiesel fuel production by supercritical methanol treatment," Bioresource Technology, vol. 91, 2004, pp. 289-295 (7 pages).
"Kyte Centrifuge Sales & Consulting," www.kcentrifuge.com, 2004 (1 page).
Lewkowitsch, J. "The Meaning of the Acetyl Value in fat Analysis," Chem. Zentr., vol. 1, 1899, pp. 375-376 (13 pages).
Li, Lixiong et al., "Catalytic Hydrothermal Conversion of Triglycerides to Non-ester Biofuels," Energy Fuels, vol. 24, 2010, pp. 1305-1315 (11 pages).
Li, Wei et al., "Study on Acyl Migration Kinetics of Partial Glycerides: Dependence on Temperature and Water Activity," Journal of Molecular Catalysis B: Enzymatic, vol. 63, 2010, pp. 17-22 (6 pages).
Liu, Yijun et al., "Transesterification of Poultry Fat with Methanol Using Mg—Al Hydrotalcite Derived Catalysts," Applied Catalysis A: General (Abstract only) 2007, vol. 331, 138-148 (2 pages).
Lopez, D.E. et al., "Transesterification of Triacetin with Methanol on Solid Acid and Base Catalysts," Appl. Catalysis A: General 2005, 295: 97-105 (9 pages).

(56) References Cited

OTHER PUBLICATIONS

Lopez, Dora E. et al., "Esterification and transesterification on tungstated zirconia: Effect of calcination temperature," Journal or Catalysis Apr. 1, 2007, vol. 247, Iss. 1, 43-50 (2 pages).
Lopez, Dora E. et al., "Esterification and transesterification using modified-zirconia catalysts," Applied Catalysis A: General, vol. 339, 2008, pp. 76-83 (8 pages).
Lotero, E. et al., "Synthesis of Biodiesel Via Acid Catalysis," Ind. Eng. Chem. Res. 2005, 44:5353-5363 (11 pages).
Lu, Jike et al., "Immobilized lipase Candida sp. 99-125 catalyzed methanolysis of glycerol trioleate: Solvent effect," Bioresource Technology, vol. 99, 2008, pp. 6070-6074 (5 pages).
Lusvardi, Victor S. et al., "The Effects of Bulk Titania Crystal Structure on the Adsorption and Reaction of Aliphatic Alcohols," Journal of Catalysis, vol. 153, 1995, pp. 41-53 (13 pages).
Ma, Ret al., "Biodiesel Production: A Review," Bioresource Technol. 1999, 70:1-15 (15 pages).
Madsen, Anders T. et al., "Step Changes and Deactivation Behavior in the Continuous Decarboxylation of Stearic Acid," Ind. Eng. Chem. Res., vol. 50, 2011, pp. 11049-11058 (10 pages).
Maher, Kelly D. et al., "Pyrolytic Decarboxylation and Cracking of Stearic Acid," Ind. Eng. Chem. Res., vol. 47, 2008, pp. 5328-5336 (9 pages).
Martinez, Jose L. et al., "Effect of Water on Canola oil Hydrolysis in an Online Extraction-Reaction System Using Supercritical Co2," Ind. Eng. Chem. Res., vol. 41, 2002, pp. 6475-6481 (7 pages).
Mazzieri, V.M. et al., "Non-Catalytic Biodiesel Process with Adsorption-Based Refining," Fuel, vol. 90, 2011, pp. 1186-1196 (9 pages).
Mcneff, Clayton V. et al., "Continuous Production of 5-Hydroxymethylfurfural from Simple and Complex Carbohydrates," Applied Catalysis A: General, vol. 384, Issues 1-2, Aug. 2010, pp. 65-69 (5 pages).
Melero, Juan A. et al., "Acidic Mesoporous Silica for the Acetylation of Glycerol: Synthesis of Bioadditives to Petrol Fuel," Abstract only, Energy & Fuels 2007, 21: pp. 1782-1791 (1 page).
Melero, Juan a. et al., "Production of Biofuels via the Catalytic Cracking of Mixtures of Crude Vegetable Oils and Nonedible Animal Fats with Vacuum Gas Oil," Energy Fuels, vol. 24, 2010, pp. 707-717 (11 pages).
"Mexico Office Action," from MX Application No. MX/a/2009/008612, dated Jul. 11, 2012, (pp. 1-4) Including English translation, (4 pages).
"Mexico Office Action," from MX Application No. MX/a/2009/008683, dated Oct. 10,2012 (pp. 1-2) Including English translation (3 pages).
Miller, Dennis J. et al., "Catalysis for Biorenewables Conversion," National Science Foundation Workshop Report www.egr.msu.edu/apps/nsfworkshop Apr. 13, 2004, 1-63 (web) (63 pages).
Minami, Eiji et al., "Kinetics of hydrolysis and methyl esterification for biodiesel production in two-step supercritical methanol process," Fuel, vol. 85, 2006, pp. 2479-2483 (5 pages).
Mittelbach, Martin et al., "Diesel Fuel Derived from Vegetable Oils, III. Emission Tests Using Methyl Esters of Used Frying Oil," JAOCS Jul. 1988, vol. 65, No. 7, 1185-1187 (3 pages).
Mohan, Dinesh et al., "Pyrolysis of wood/Biomass for Bio-Oil: A Critical Review," Energy and Fuels, vol. 20, 2006, pp. 848-889 (42 pages).
Moquin, Paul H. et al., "Kinetic modeling of hydrolysis of canola oil in supercritical media," Journal of Supercritical Fluids, vol. 45, 2008, pp. 94-101 (8 pages).
Moreau, C. et al., Applied Catalysis A:General vol. 145, No. 1-2, XP002454168 tables 1, 3 1996, pp. 211-224 (14 pages).
Murkute, Ambareesh D. et al., "Supported Mesoporous Solid Base Catalysts for Condensation of Carboxylic Acids," Journal of Catalysis, vol. 278, 2011, pp. 189-199 (11 pages).
Na, J. et al., "Hydrocarbon Production from Decarboxylation of Fatty Acid without Hydrogen," Catalysis Today, vol. 156, 2010, pp. 44-48 (5 pages).
Nawrocki, J. et al., "Chemistry of Zirconia and Its Use in Chromatography," J. Chromatog. 1993, A 657: 229-282 (54 pages).
"New Process Makes Diesel Fuel and Industrial Chemicals from Simple Sugar," College of Engineering University of Wisconsin-Madison, http://www.engr.wisc.edu/news/headlines/2006/Jun29a.html 1 of 3 Jun. 18, 2008 9:28 AM Jun. 29, 2006 (3 pages).
Ngaosuwan, Kanokwan et al., "Effect of solvent on hydrolysis and transesterification reactions on tungstated zirconia," Applied Catalysis A: General, vol. 380, 2010, pp. 81-86 (6 pages).
Ngaosuwan, Kanokwan et al., "Hydrolysis of Triglycerides Using Solid Acid Catalysts," Ind. Eng. Chem. Res, vol. 48, 2009, 4757-4767 (11 pages).
Ngaosuwan, Kanokwan et al., "Reaction Kinetics and Mechanisms for Hydrolysis and Transesterification of Triglycerides on Tungstated Zirconia," Top Catal, vol. 53, 2010, pp. 783-794 (12 pages).
"Non-Final Office Action," for Mexican Patent Application No. MX/a/2010/000135, dated Mar. 3, 2014 (2 pages).
"Notice of Allowance," for Canadian Patent Application No. 2660049, dated Mar. 23, 2015 (1 page).
"Notice of Allowance," from MX Application No. MX/a/2009/001280, corresponding to U.S. Appl. No. 60/821,498, dated May 3, 2011, (pp. 1-2) (2 pages).
O'connor, Charmian J. et al., "Determining the regio- and typoselectivity of calf pregastric lipase," Journal of Molecular Catalysis B: Enzymatic, vol. 16, 2001, pp. 147-157 (11 pages).
"Office Action," for CA Application No. 2660049, dated May 8, 2014 (2 pages).
"Office Action," for Canadian Patent Application No. 2,691,545, dated Jan. 31, 2014 (2 pages).
"Office Action," for Canadian Patent Application No. 2,765,043, dated May 18, 2016 (4 pages).
"Office Action," for Mexican Application No. MX/a/2011/013275, dated Jun. 19, 2013 (3 pages).
"Office Action," from CA Application No. 2660049, dated Jun. 28, 2013 (2 pages).
Omota, F. et al., "Fatty Acid Esterification by Reactive Distillation: Part 2—Kinetics-based Design for Sulphated Zirconia Catalysts," Chemical Engineering Science 2003, 58: 3175-3185 (11 pages).
Ondrey, G. "Biodiesel Production Using a Heterogeneous Catalyst," Chemical Engineering 2004, 111(11):13 (1 page).
Ooi, Yean Sang et al., "Catalytic Cracking of Used Palm Oil and Palm Oil Fatty Acids Mixture from the Production of Liquid Fuel: Kinetic Modeling," Energy & Fuels, vol. 18, 2004, pp. 1555-1561 (7 pages).
Otera, J. "Transesterification," Chem. Rev. 1993, 93:1449-1470 (22 pages).
Palanisamy, Shanmugam et al., "Thermal Treatment of Rapeseed Oil," Bioenergy Technology, 2011, pp. 546-551 (6 pages).
Pariente, Stephane et al., "Etherification of glycerol with ethanol over solid acid catalysts," 2008, Green Chern., 11, 1256-1261 (6 pages).
Parve, Omar et al., "Lipase-Catalysed Enantioselective Hydrolysis: Interpretation of the Kinetic Results in Terms of Frontier Orbital Localisation," Tetrahedron, vol. 53, 1997, pp. 4889-4900 (12 pages).
Patel, Akshay D. et al., "Techno-Economic Analysis of 5-Nonanone Production from Levulinic Acid," Chemical Engineering Journal, vol. 1, 2010, pp. 311-321 (11 pages).
PCT International Search Report and Written Opinion from International Application No. PCT/US2007/075211, dated Jul. 9, 2008 (10 pages).
PCT International Search Report and Written Opinion from International Application No. PCT/US2010/038000 dated Oct. 4, 2010 (13 pages).
"PCT International Search Report and Written Opinion," from International Application No. PCT/US2008,068188, dated Sep. 3, 2008 (15 pages).
"PCT International Search Report and Written Opinion," from International Application No. PCT/US2009069280, dated Sep. 13, 2010 (20 pages).
"PCT International Search Report and Written Opinion," PCT International Search Report and Written Opinion from International Application No. PCT/US2008/053844, dated Aug. 6, 2008 (14 pages).

(56) References Cited

OTHER PUBLICATIONS

"PCT Notification Concerning Transmittal of International Preliminary Report on Patentability" from International Application No. PCT/US2009/069280, dated Jul. 7, 2011 (12 pages).
"PCT Notification Concerning Transmittal of International Preliminary Report on Patentability," From International Application No. PCT/US2007/075211, dated Feb. 19, 2009 (9 pages).
"PCT Notification Concerning Transmittal of International Preliminary Report on Patentability," from International Application No. PCT/US2008/053844, dated Aug. 27, 2009 (7 pages).
"PCT Notification Concerning Transmittal of International Preliminary Report on Patentability," from International Application No. PCT/US2008/068188, dated Jan. 5, 2010 (8 pages).
"PCT Notification Concerning Transmittal of International Preliminary Report on Patentability," From International Application No. PCT/US2008053883, dated Aug. 27, 2009 (9 pages).
"PCT Notification Concerning Transmittal of International Preliminary Report on Patentability," from International Application No. PCT/US2010/38000, dated Dec. 22, 2011 (6 pages).
Pei, Z. F. et al., "On the Intermediates of the Acetic Acid Reactions on Oxides: An IR Study," Applied Surface Science, vol. 103, 1996, pp. 171-182 (12 pages).
Perlack, Robert D. et al., "Biomass as Feedstock for Bioenergy and Bioproducts Industry: Technical Feasibility of a Billion-Ton Annual Supply," U.S. Department of Agriculture Apr. 2005 (78 pages).
Peterson, Andrew A. et al., "Thermochemical Biofuel Production in Hydrothermal Media: a Reivew of Sub- and Supercritical Water Technologies," Energy and Environmental Science, 2008, 1, pp. 32-65 (34 pages).
Peterson, C. L. et al., "Continuous Flow Biodiesel Production," Appl. Eng. Agricul. 2002, 18: 5-11 (7 pages).
Petkewich, Rachel "Sweet Routes to Sustainability: Catalytic reactions converts sugars from biomass into renewable fuel and feedstock," Cnemical & Engineering News, http://pubs.acs.org/cen/news/85/i26/8526notw1.html Jun. 25, 2007, V. 85, No. 26, p. 8 (3 pages).
Pinto, a. C. et al., "Biodiesel: An Overview," J. Braz. Chem. Soc. 2005, 16: 1313-1330 (18 pages).
Piyatheerawong, Weera et al., "Enzymatic Preparation of Enantiomerically Pure sn-2, 3-Dicylglycerols: A Stereoselective Ethanolysis Approach," JAOCS, vol. 83, 2006, pp. 603-607 (5 pages).
Priecel, Peter et al., "The Role of Ni Species in the Deoxygenation of Rapeseed Oil Over NiMo-Alumina Catalysts," Applied Catalysis A: General, vol. 397, 2011, 127-137 (11 pages).
Pruszko, R. "Strategic Biodiesel Decisions," Iowa State University—University Extension CIRAS 2006, 1-32 (32 pages).
Qi, Zhang et al., "Review of bioMass Pyrolysis Oil Properties and Upgrading Research," Energy Conversion and Management vol. 48, 2007, pp. 87-92 (6 pages).
Qi., X. et al., "Catalysis Communications," vol. 9, No. 13, XP022824415 p. 2245, paragraph 2.2; tables 1-3,table 2 Jul. 20, 2008, pp. 2244-2249 (6 pages).
"Qualitative and Quantitative Analysis in GC and GCMS," Customer Support Centre, Shimadzu Asia Pacific Pte. Ltd., 2006, Singapore (32 pages).
Quirino, Rafael L. et al., "Studying the Influence of Alumina Catalysts Doped with Tin and Zinc Oxides in the Soybean Oil Pyrolysis Reaction," J AM Oil Chem Soc, vol. 86, 2009, pp. 167-172 (6 pages).
Raddi De Araujo, Lucia R. et al., "H3PO4/Al2O3 Catatysts: Characterization and Catalytic Evaluation of Oleic Acid Conversion to Biofuels and Biolubricant," Materials Research 2006, vol. 9, No. 2, 181-184 (4 pages).
Reisch, Marc S. "Start-up Firms Pursue Biofuels," Chemical & Engineering News Nov. 20, 2006, vol. 84, No. 47, 1-2(web) (2 pages).
Renz, Michael "Ketonization of Carboxylic Acids by Decarboxylation: Mechanism and Scope," Eur. J. Org. Chem., 2005, pp. 979-988 (10 pages).
"Response to Mexico Office Action," dated Oct. 30, 2012 for MX Application No. MX/a/2009/008612 (8 pages).
"Response to Office Action," for Canadian Patent Application No. 2,660,049, dated May 8, 2014 and filed with the CIPO Nov. 6, 2014 (5 pages).
Rigney, M. P. et al., "Physical and Chemical Characterization of Microporous Zirconia," J. Chromatog 1990, 499: 291-304 (14 pages).
Robichaud, Michael J. et al., "An Improved Oil Emulsion Synthesis Method for Large, Porous Zirconia Particles for Packed- or Fluidized-Bed Protein Chromatography," Separation Science and Technology, vol. 32, 1997, pp. 2547-2559 (7 pages).
Ruan, Roger et al., "Size matters: small distributed biomass energy production systems for economic viability," Int J Agric & Biol Eng Aug. 2008, vol. 1 No. 1, pp. 64-68 (5 pages).
Saka, Shiro et al., "Useful Products from Lignocellulosics by Supercritical Water Technologies," The 2nd Joint International Conference on "Sustainable Energy and Environment (SEE 2006)," Nov. 2006 (5 pages).
Sassi, "Methanol to hydrocarbon catalysis on sulfated zirconia proceeds through a hydrocarbon-pool mechanism," Catalysis Letters, 81(1-2):101-105 (2002) (5 pages).
Schmid, U. et al., "Highly Selective Synthesis of 1,3-Oleoyl-2-Palmitoylglycerol by Lipase Catalysis," Biotechnology and Bioengineering, vol. 64, 1999, pp. 678-684 (7 pages).
Schuchardt, Ulf et al., "Transesterification of Vegetable Oils: a Review," J. Braz. Chem. Soc. 1998, vol. 9, No. 1, 199-210 (12 pages).
Serrano-Ruiz, Juan Carlos et al., "Catalytic Upgrading of Lactic Acid to Fuels and Chemicals by Dehydrations/Hydrogenation and C-C Coupling Reactions," Green Chem., vol. 11, 2009, pp. 1101-1104 (5 pages).
Serrano-Ruiz, Juan Carlos et al., "Catalytic Upgrading of Levulinic Acid to 5-Nonanone," Green Chem., vol. 12, 2010, pp. 574-577 (4 pages).
Serrano-Ruiz, Juan Carlos et al., "Transformation of Biomass-Derived Platform Molecules: From High Added-Value Chemicals to Fuels via Aqueous-Phase Processing," Chemical Society Reviews, vol. 40, pp. 5266-5281 (16 pages).
Shanks, Brent H. "Conversion of Biorenewable Feedstocks: New Challenges in Heterogeneous Catalysis," Ind. Eng. Chem. Res., vol. 49, 2010, pp. 10212-10217 (6 pages).
Shieh, Chwen-Jen et al., "Optimized Enzymatic Synthesis of Geranyl Butyrate with Lipase AY from Candida Rugosa," Biotechnology and Bioengineering, vol. 51, 1996, pp. 371-374 (4 pages).
Silva, Lisa et al., "Colorado Diesel School Bus Retrofit Program," A Cooperative Effort of the Regional Air Quality Council and the Colorado Department of Public Health and Environment 2006, 1-17 (17 pages).
Simonetti, Dante A. et al., "Catalytic Production of Liquid Fuels from Biomass-Derived Oxygenated Hydrocarbons: Catalytic Coupling at Multiple Length Scales," Catalysis Reviews, vol. 51, 2009, pp. 441-484 (45 pages).
Siswanto, Dessy Y. et al., "Gasoline Production from Palm Oil Via Catalytic Cracking Using MCM-41: Determination of Optimum Condition," Journal of Engineering and Applied Sciences, vol. 3, 2008, pp. 42-46 (5 pages).
Stefanidis, S.D. et al., "In-Situ Upgrading of Biomass Pyrolysis Vapors: Catalyst Screening on a Fixed Bed Reactor," Bioresource Technology, vol. 102, 2011, pp. 8261-8267 (7 pages).
Steinbusch, Kirsten J. et al., "Biological Formation of Caproate and Caprylate from Acetate: Fuel and Chemical Production from Low Grade Biomass," Energy Environ. Sci., vol. 4, 2011, p. 216 (9 pages).
Su, Yu et al., "Single Step Conversion of Cellulose to 5-hydroxymethylfurfural (HMF), a Versatile Platform Chemical," Applied Catalysis A: General, 361 Apr. 9, 2009, 117-122 (6 pages).
Suib, Steven L. "New and Future Developments in Catalysis," Catalytic Biomass Conversion, p. 184, ISBN: 978-0-444-53878-9 (1 page).
Suppes, G. J. et al., "Transesterification of Soybean Oil with Zeolite and Metal Catalysts," Applied Catalysis A: General 2004, 257: 213-223 (11 pages).

(56) References Cited

OTHER PUBLICATIONS

Suwannakarn, Kaewta et al., "A comparative study of gas phase esterification on solid acid catalysts," Catalysis Letters Apr. 2007, vol. 114, Nos. 3-4 (7 pages).
Swaminathan, R. et al., "Studies on the Ketonization of Acetic Acid on Chromia: II. The Surface Reaction," Journal of Catalysis, vol. 16, 1970, pp. 357-362 (6 pages).
Takahashi, Yoshinori et al., "Characteristics of Lipase Modified with Water-soluble Acylating Reagents and Its Esterification Ability," Biosci. Biotech. Biochem., vol. 59, 1995, pp. 809-812 (4 pages).
Tamunaidu, Pramila et al., "Catalytic Cracking of Palm Oil for the Production of Biofuels: Optimization Studies," Bioresource Technology, vol. 98, 2007, pp. 3593-3601 (9 pages).
Tanksale, Akshat et al., "A Review of catalytic Hydrogen production Processes from Biomass," Renewable and Sustainable Energy Reviews, vol. 14, 2010, pp. 166-182 (17 pages).
Tanner, R.E. et al., "Structure and Chemical Reactivity of Adsorbed Carboxylic Acids on Anatase TiO2(001)," Surface Science, vol. 506, 2002, pp. 251-271 (21 pages).
Tavakoli, Omid et al., "Squid Oil and Fat Production from Squid Wastes Using Subcritical Water Hydrolysis: Free Fatty Acids and Transesterification," Ind. Eng. Chem. Res., vol. 45, 2006, pp. 5675-5680 (6 pages).
Ten Dam, Jeroen et al., "Renewable Chemicals: Dehydroxylation of Glycerol and Polyols," ChemSusChem, vol. 4, 2011, pp. 1017-1034 (18 pages).
Toor, Saqib S. et al., "Hydrothermal Liquefaction of Biomass: A Review of Subcritical Water Technologies," Energy 36 (2011), pp. 2328-2342 (15 pages).
Twaiq, Farouq A. et al., "Liquid Hydrocarbon Fuels from Palm Oil by Catalytic Cracking Over Aluminosilicate Mesoporous Catalysts with Various Si/Al ratios," Microporous and Mesoporous Materials, vol. 64, 2003, pp. 95-107 (13 pages).
Tyson, K. S. "Brown Grease Feedstocks for Biodiesel," National Renewable Energy Laboratory Jun. 19, 2002, 1-34 (34 pages).
Ulgen, Arda et al., "Conversion of Glycerol to Acrolein in the Presence of WO3/TiO2 Catalysts," Applied Catalysis A; General 400 (2011) pp. 34-38 (5 pages).
Unknown, "AMBERLITEtm FP Ion Exchange Resins," Amberlite FP technical bulletin http://www.advancedbiosciences.com Dec. 2004, 1-7 (7 pages).
Unknown, "Standard Test Method for Acid Number of Petroleum Products by Potentiometric Titration," ASTM International, Designation: D664-04 Mar. 2004, 1-7 (7 pages).
Unknown, et al., "Oak Ridge lab develops materials for biodiesel catalysis," Biodiesel Magazine http://biodieselmagazine.com/article-print.jsp?article_id=1580 2007 (1 page).
Van Tol, J. B. et al., "Do Organic Solvents Affect the Catalytic Properties of Lipase? Intrinsic Kinetic Parameters of Lipases in Ester Hydrolysis and Formation in Various Organic Solvents," Biotechnology and Bioengineering, vol. 47, 1995, pp. 71-81 (11 pages).
Varma, Mahesh N. et al., "Effect of Chain Length on Enzymatic Hydrolysis of p-Nitrophenyl Esters in Supercritical Carbon Dioxide," Appl Biochem Biotehnol, vol. 144, 2008, pp. 213-223 (11 pages).
Verkade, J. G. et al., "Nanoporous Solid Catalysts for Conversion of Soybean Oil to Biodiesel," Center for Catalysis, Iowa State University http://www.iprt.iastate.edu/ccat/nano.html Feb. 22, 2006, 1-4 (4 pages).
Vieitez, Ignacio et al., "Continuous catalyst-free methanolysis and ethanolysis of soybean oil under supercritical alcohol/water mixtures," Renewable Energy, vol. 35., 2010, pp. 1976-1981 (6 pages).
Vieitez, Ignacio et al., "Continuous Production of Soybean Biodiesel in Supercritical Ethanol-Water Mixtures," American Chemical Society, Energy & Fuels Jun. 17, 2008, pp. 1-5 (5 pages).
Vivier, Laurence et al., "Ceria-Based Solid Catalysts for Organic Chemistry," ChemSusChem, vol. 3, 2010, pp. 654-678 (25 pages).
Vonghia, Enrico et al., "Pathways for the Deoxygenation of Triglycerides to Aliphatic Hydrocarbons over Activated Alumina," Energy & Fuels, vol. 9, 1995, pp. 1090-1096 (7 pages).
Watanabe, et al., Carbohydrate Research 340 (2005) 2005, 1925-1930 (6 pages).
Watanabe, Masaru et al., "Catalytic Hydrogen Generation from Biomass (Glucose and Cellulose) with ZrO2 in Supercritical Water," Biomass and Bioenergy 2002, 22, 405-410 (6 pages).
White, D. H. et al., "Development of an Extruder-Feeder Biomass Direct Liquefactoin Process," Final Report, vol. 1, Oct. 1991, Parts 1-3 (294 pages).
White, Don H. et al., "Biomass Liquefaction Utilizing Extruder-Feeder Reactor System," Department of Chemical Engineering, University of Arizona, date unknown, pp. 106-116 (11 pages).
Wiggers, et al., "Biofuels from continuous fast pyrolysis of soybean oil: A pilot plant study," Bioresource Technology, vol. 100, (2009) pp. 6570-6577. (8 pages).
Xie, W. et al., "Synthesis of Biodiesel from Soybean Oil Using Heterogeneous KF/ZnO Catalyst," Catalyst Letters Feb. 2006, 107: 53-59 (7 pages).
Xu, M. et al., "Synthesis of Dimethyl Ether (DME) from Methanol Over Solid-Acid Catalysts," Applied Catalysis A: General 149, Elsevier, Science, Amsterdam, NL, vol. 149, No. 2, pp. 289-301 Feb. 6, 1997 (14 pages).
Yalpani, M. "Alterations of Polysaccharide Intergrity and Electrochemical Modifications," Polysaccharides. Syntheses, Modifications and Structure Jan. 1, 1988, 370-4004 (35 pages).
Yamakawa-Kobayashi, Kimiko et al., "Relation of the -514C/T Polymorphism in the Hepatic Lipase Gene to Serum HDL and LDL Cholesterol Levels in Postmenopausal Women Under Hormone Replacement Therapy," Atherosclerosis, vol. 162, 2002, pp. 17-21 (5 pages).
Yared, Ivan et al., "Modeling of Liquid hydrocarbon Fuel Production from Palm Oil Via Catalytic Cracking Using MCM-41 as Catalyst," Journal of Engineering and Applied Sciences, vol. 3, 2008, pages (7 pages).
Yean Sang, Ooi "Biofuel Production from Catalytic Cracking of Palm Oil," Energy Sources, vol. 25, 2003, pp. 859-869 (12 pages).
Yokoyama, Shin-Ya et al., "Liquid Fuel Production from Ethanol Fermentation Stillage," Chemistry Letters 1986, pp. 649-652 (4 pages).
Yu, Fei et al., "Liquefaction of Corn Cobs with Supercritical Water Treatment," American Society of Agricultural and Biological Engineers 2007, vol. 50(1): 175-180 (6 pages).
Yu, Fei et al., "Liquefaction of Corn Stover and Preparation of Polyester from the Liquefied Polyol," Applied Biochemistry and Biotechnology 2006, vol. 129-132, pp. 574-585 (12 pages).
Yu, Fei et al., "Physical and Chemical Properties of Bio -Oils From Microwave Pyrolysis of Corn Stover," Applied Biochemistry and Biotechnology 2007, vol. 136-140, pp. 957-970 (14 pages).
Yu, Fei et al., "Reaction Kinetics of Stover Liquefaction in Recycled Stover Polyol," Applied Biochemistry and Biotechnology 2006, vol. 129-132 pp. 563-573 (11 pages).
Yu, Yang et al., "Enzymatic Synthesis of Feruloyated Lipids: Comparison of the Efficiency of Vinyl Ferulate and Ethyl Ferulate as Substrates," J AM Oil Chem Soc, vol. 87, 2010, pp. 1443-1449 (7 pages).
Zhang, P. "A New Process for Biodiesel Production Based on Waste Cooking Oils and Heterogeneous Catalysts," USDA-SBIR Agreement #2005-33610-15497 2005, 1-2 (2 pages).
Zheng, Yan et al., "Dual Response Surface-Optimized Process for Feruloylated Diacylglycerols by Selective Lipase-Catalyzed Transesterification in Solvent Free System," Bioresource Technology, vol. 100, 2009, pp. 2896-2901 (6 pages).

SYSTEMS AND METHODS FOR SYNTHESIS OF PHENOLICS AND KETONES

This application claims the benefit of U.S. Provisional Application No. 62/491,021, filed Apr. 27, 2017, the content of which is herein incorporated by reference in its entirety.

FIELD

Embodiments herein relate to apparatus and systems for phenolic and ketone synthesis and methods regarding the same.

BACKGROUND

Cellulose is one of the most ubiquitous and important natural carbohydrate polymers on earth. Cellulose is a linear biopolymer found in plant cells such as trees, plants, and algae. Cellulose is a polysaccharide made up of many thousands of glucose units and is known as poly 1,4-β-D-glucose. Cellulose has the general formula $(C_6H_{10}O_5)_n$. The lignin, hemicellulose, and cellulose configurations found in plant cells make the β linkages in the cellulose polymer difficult to access and cleave. This feature, along with the ability to form long hydrogen-bonded fibers, makes cellulose a stable and strong material for plant structures. The following figure shows the chemical structure of cellulose where individual glucose units are linked in the β-position.

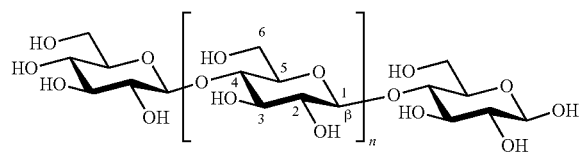

Phenolics and ketones are a class of important industrial chemicals that are widely used in the polymer, adhesives, and solvent markets. The current large-scale production of phenol mostly uses the cumene process, also known as the cumene-phenol or Hock process. In the cumene process, the starting materials benzene and propylene are first converted to cumene and then subsequently to phenol with coproduction of an equimolar byproduct of acetone. The benzene and propylene starting materials are derived from the non-renewable petroleum industry on the scale of tens of millions of tons per year, which means that the process is not considered sustainable.

SUMMARY

Embodiments herein relate to apparatus and systems for phenolic and ketone synthesis and methods regarding the same. In an embodiment, a method of producing phenolics and ketones is included. The method can specifically include forming a reaction mixture comprising nanocrystalline cellulose (NCC) and water. The method can also include contacting the reaction mixture with a metal oxide catalyst at a temperature of 350 degrees Celsius or higher and a pressure of at least about 3200 psi to form a reaction product mixture. The reaction product mixture can include at least about 20 wt. % phenolics and at least about 10 wt. % ketones as a percentage of the total mass of nanocrystalline cellulose (NCC).

In an embodiment, an apparatus for producing a reaction product mixture including phenolics and ketones is included. The apparatus can include a feedstock tank comprising a nanocrystalline cellulose (NCC) feedstock; a water supply line; a reactor vessel in direct or indirect fluid communication with the feedstock tank and the water supply line; a plurality of metal oxide catalyst particles disposed within the reactor vessel; a heating element; and a back pressure regulator in fluid communication with the reactor vessel.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

BRIEF DESCRIPTION OF THE FIGURES

Aspects may be more completely understood in connection with the following drawings, in which.

While embodiments are susceptible to various modifications and alternative forms, specifics thereof have been shown by way of example and drawings, and will be described in detail. It should be understood, however, that the scope herein is not limited to the particular embodiments described. On the contrary, the intention is to cover modifications, equivalents, and alternatives falling within the spirit and scope herein.

DETAILED DESCRIPTION

As discussed herein, cellulose represents vast potential as a raw material in the production of sustainable materials on an industrial scale. Cellulose is a sustainable resource, in that it has the ability to be perpetually produced from renewable materials. Nanocrystalline cellulose (NCC) is a submicron sized nanoparticle obtained from the acid hydrolysis of cellulose. Suspensions of NCC in aqueous solutions can be fluidic and are well suited to enter micron-sized pores of a metal oxide catalyst bed.

As disclosed herein, it has been discovered that certain metal oxides can be used to catalyze the reaction of NCC into industrially useful phenolic and ketone products using a sustainable and continuous catalytic reaction process. In some embodiments, the process disclosed herein can convert at least about 50% by weight of the total starting mass of NCC into liquid and solid reaction products. In some embodiments, the process disclosed herein can convert at least about 50% by weight of the total starting mass of NCC into a mixture of carbon dioxide, methane, and ethylene gases.

The term "phenolics" as used herein refers to a class of molecules having one or more hydroxyl groups (—OH) attached to an aromatic ring (e.g., hydroxybenzene in the case of phenol). In some embodiments, phenolics can include polyphenol compounds having one or more diaryl ether links (i.e., Ar—O—Ar') produced by dehydration of two or more phenols. The term "ketones" as used herein refers to a class of molecules containing the carbonyl functional group (i.e., a carbon-oxygen double bond (C=O)) and two alkyl or aryl groups attached to the carbonyl carbon.

Embodiments herein can produce a product mixture that includes a remarkably high proportion of phenolics and ketones. By way of example, of the liquid portion of the product mixture (at ambient temperature and pressure such as 23 degrees Celsius and 760 mmHg), without an additional separation step applied to the liquid portion, at least about 50, 60, 70, 80, 85, 90, 92, 94, 95, 96, 97, 98, 99 or 99.5 wt. % can be phenolics and ketones. In some embodiments the amount of phenolics and ketones in the liquid portion of the product mixture can be in a range wherein any of the forgoing amounts can serve as the lower bound of the range and the upper bound of the range can be 100 wt. % or 99.9 wt. %.

Reactor Systems

Figure 1:
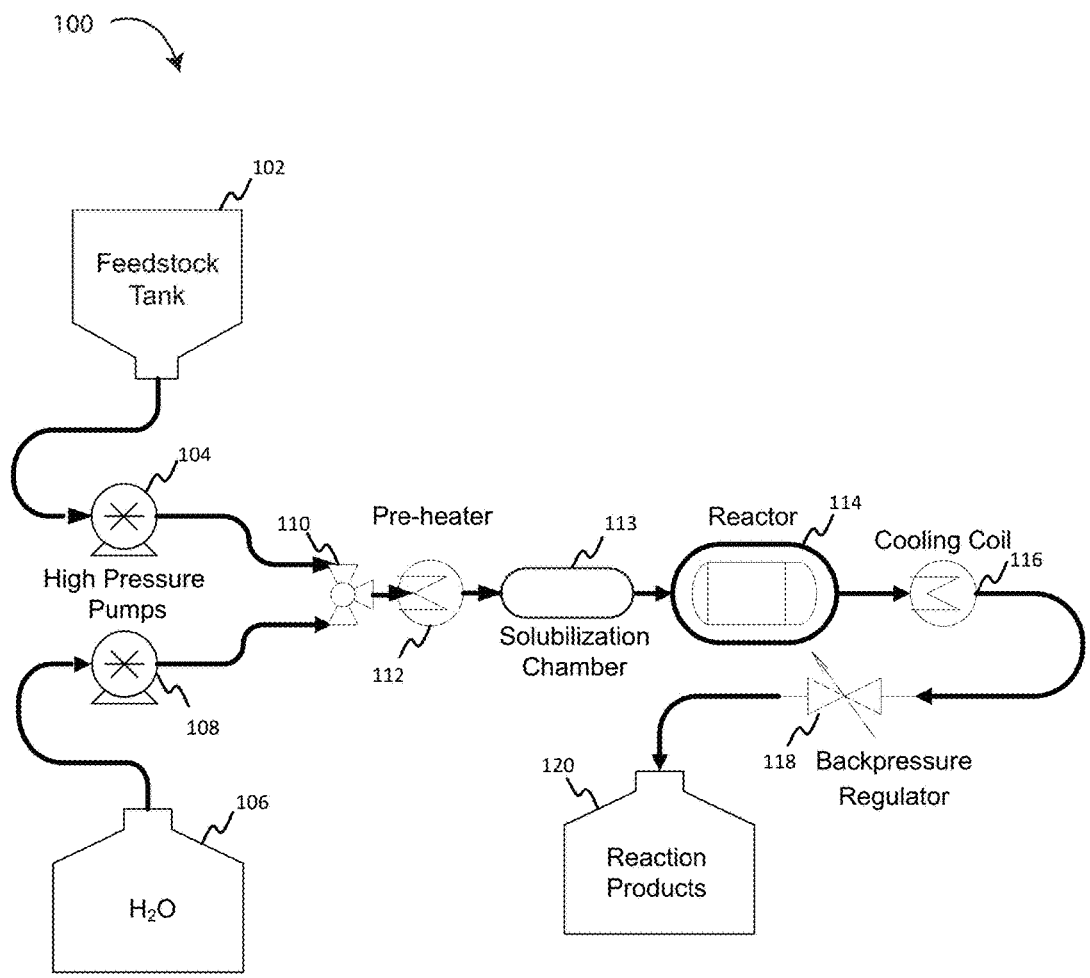
FIG. 1 is a schematic diagram of a reactor system in accordance with the embodiments herein.

Referring now to FIG. 1, a schematic view of a basic reactor 100 is presented in accordance with the embodiments herein. An aqueous slurry of NCC can be held in feedstock tank 102. Various examples of sources for obtaining NCC as embodied herein are discussed below in more detail. A co-reactant, such as water, can be held in a second feedstock tank 106 to act as a water supply line. One or both of the tanks can be continuously sparged with an inert gas such as nitrogen to remove dissolved oxygen from the respective reactants. While this embodiment of a reactor setup includes two separate feedstock tanks, it will be appreciated that in some embodiments only a single feedstock tank can be used and the reactants can be combined together within the single feedstock tank. Similarly, it will be appreciated that more than two separate feedstock tanks can be used. For example, additional co-reactants such as lipids, proteins, carbohydrates, algae, and the like can also be used in some embodiments and can be disposed within one or more additional feedstock tanks.

The aqueous slurry of NCC, and co-reactant (if present), can then pass from the first feedstock tank 102 and second feedstock tank 106 through high pressure pumps 104 and 108, respectively, before being combined and passing through a heat exchanger (not shown) where the reactants can absorb heat from downstream products. The reactant mixture can then pass through a shutoff valve 110 and, optionally, a filter (not shown).

In some embodiments, a solubilization chamber 113 can be inserted into the reactor 100 between feedstock tanks 102 and 106 and the reactor vessel 114. In the solubilization chamber 113, the NCC can be mixed with water and heated to a temperature of greater than 100 degrees Celsius to form the reaction mixture just prior to contacting the metal oxide catalyst in reactor vessel 114. It will be appreciated that various components can be removed or inserted anywhere along the path of the reactor system, as will be discussed in more detail below with reference to FIG. 3.

The feedstock mixture can then pass through a preheater 112 and into a reactor vessel 114 where the reactant mixture is converted into a reaction product mixture. Reactor vessel 114 can be in direct or indirect fluid communication with the NCC slurry feedstock tank and water supply line. The reactor vessel can include a catalyst, such as in the various forms described herein. In some embodiments, the catalyst can be in the form of a plurality of metal oxide particles and it can be packed within the reactor vessel as a fixed-bed catalyst. It will be appreciated that, the reactor vessel can be configured to accommodate industrial scale processing of equal to or greater than 50, 100, 1000, 10,000 or more kg of NCC per 24 hour period.

The reaction product mixture can pass through the heat exchanger (not shown) in order to transfer heat from the effluent reaction product stream to the feedstock streams. In some embodiments, the reaction product mixture can pass through a cooling coil 116. The liquid reaction product mixture can also pass through a backpressure regulator 118 before passing on to a liquid reaction product storage tank 120. In some embodiments, the reaction products can include a gaseous phase that is collected in a separate chamber.

In some embodiments, at least about 5, 10, 15, 20, 30, 40, 50, 60, 70, 80, 90, 95 or 98 wt. percent of the reaction product mixture is in a liquid form (at ambient temperature and pressure conditions such as 23 degrees Celsius and 760 mmHg). In some embodiments, the amount of the reaction product mixture that is in a liquid form is in a range wherein any of the foregoing can serve as the lower or upper bound of the range, provided that the upper bound is greater than the lower bound.

Figure 2:
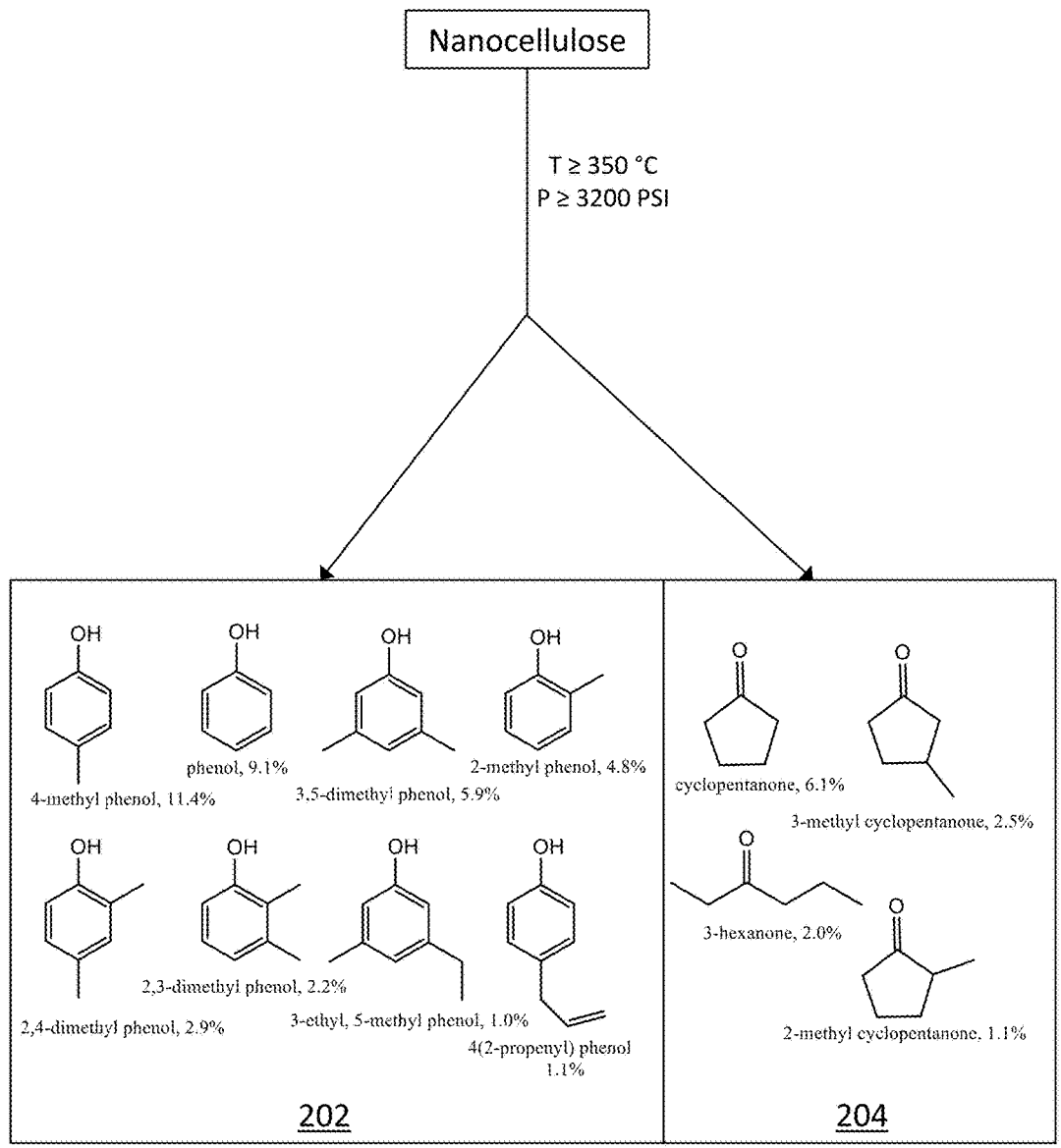
FIG. 2 is a schematic diagram of the conversion of nanocrystalline cellulose (NCC) into exemplary phenolic and ketone reaction products in accordance with various embodiments herein.

Referring now to FIG. 2, schematic diagram of the conversion of NCC into exemplary phenolic 202 and ketone 204 reaction products is shown. As NCC is treated at supercritical water conditions (i.e., T≥350 degrees Celsius and P≥3,200 PSI) and passed over a metal oxide catalyst, a reaction product mixture of various phenolic 202 and ketone 204 products forms. FIG. 2 shows the reaction products observed through an exemplary hydrothermolytic process. Exemplary phenolics 202 can include, but are not limited to, phenol; 4-methyl phenol; 3,5-dimethyl phenol; 2-methyl phenol; 2,4-dimethyl phenol; 2,3-dimethyl phenol; 3-ethyl, 5-methyl phenol; and 4(2-propenyl) phenol. Exemplary ketones 204 can include, but not be limited to, cyclopentanone; 3-methyl cyclopentanone; 3-hexanone; and 2-methyl cyclopentanone.

While not intending to be bound by theory, it is believed that the phenolic reaction products formed during the degradation of NCC can supply protons to catalyze some of the reaction pathways leading to various phenolics and ketones produced. (Phenols are weakly acidic (Ka~1×10-10) in water and serve as a supply of protons.) Similarly, polyphenols represent a complex system of interconnected phenols such as those found in naturally occurring tannins like tannic acid. These types of structures comprise a portion of natural cellulose and they may also be formed during NCC degradation. The phenolic reaction products can be hydrothermolytically labile, thus being susceptible to cleavage into lower molecular weight, higher value phenols observed during the NCC degradation discussed herein.

It will be appreciated that various processes can be performed on the reaction products. By way of example, in some cases, a bio-coal-tar phase, (containing a mixture of mostly hydrocarbon molecules) can be separated from a phase that includes a reaction product mixture. In some embodiments, various reaction products can be separated from one another using distillation techniques. In some embodiments, the reaction products can be isolated from one another and then subjected to further reaction steps. In some embodiments, the reaction products can be analyzed using several analytical methods including: solid and non-volatile liquid products analysis by thermal gravimetric analysis (TGA) and Fourier transform infrared (FTIR) spectroscopy, liquid product analysis by gas, liquid, and mass chromatographic methods (GC-MS and HPLC) as well as NMR and FTIR methods, and gaseous products by headspace gas chromatography (HS-GCMS) along with gas phase FTIR.

Reaction Conditions

In some embodiments, an aqueous slurry of NCC can be pumped through a reaction vessel containing a packed, fixed-bed metal oxide catalyst at or above supercritical water conditions (i.e., T≥350 degrees Celsius and P≥3,200 PSI). In some embodiments, the temperature (T) can be varied from about 350 degrees Celsius to about 700 degrees Celsius. In some embodiments, the temperature can be equal to or greater than 374 degrees Celsius. In some embodiments the temperature can be between 374 degrees Celsius to 600 degrees Celsius. In some embodiments the temperature can be between 374 degrees Celsius to 525 degrees Celsius. In some embodiments the temperature can be between 500 degrees Celsius to 600 degrees Celsius. In some embodiments, the temperature can be equal to or greater than 350, 375, 400, 425, 450, 475, 500, 525, 550, 575, 600, 650, or 700 degrees Celsius. In some embodiments, the temperature can be in a range wherein any of the foregoing temperatures can serve as the upper or lower bound of the range, provided that the upper bound is greater than the lower bound.

In some embodiments, the reaction mixture is kept under pressure (P) during the entire reaction in order to prevent components of the reaction mixture from vaporizing. The reactor column can be configured to withstand the pressure under which the reaction mixture is kept. In addition, a backpressure regulator can be used to maintain a desired pressure. A desirable pressure for the reactor column can be estimated with the aid of the Clausius-Clapeyron equation. Specifically, the Clausius-Clapeyron equation can be used to estimate the vapor pressures of a liquid. The Clausius-Clapeyron equation is as follows:

$$\ln\left(\frac{P_1}{P_2}\right) = \frac{\Delta H_{vap}}{R}\left(\frac{1}{T_2} - \frac{1}{T_1}\right)$$

wherein $\Delta H_{vap}$=is the enthalpy of vaporization; $P_1$ is the vapor pressure of a liquid at temperature $T_1$; $P_2$ is the vapor pressure of a liquid at temperature $T_2$, and R is the ideal gas constant.

In some embodiments, the pressure inside the reactor column is greater than the vapor pressures of any of the components of the reaction mixture. In some embodiments, the pressure is greater than or equal to about 3200 psi. In some embodiments, the pressure is greater than or equal to about 4000 psi. In some embodiments, the pressure is greater than or equal to about 5000 psi. In some embodiments, the pressure is greater than or equal to about 6000 psi. In some embodiments, the pressure is greater than or equal to about 7000 psi. In some embodiments, the pressure can be in a range wherein any of the foregoing pressures can serve as the upper or lower bound of the range, provided that the upper bound is greater than the lower bound.

The NCC slurry mixture can be passed over the fixed-bed metal oxide catalyst for any amount of time sufficient for the reaction to reach the desired level of completion. Contact time between the NCC slurry mixture and the catalyst can depend on factors such as concentration of the NCC slurry, surface area of the catalyst, reaction temperature, reaction pressure, and the like. In some embodiments, the contact time can be between about 0.1 seconds and 10 hours. In some embodiments, the contact time can be between about 0.1 seconds and 2 hours. In some embodiments, the contact time can be between about 1 second and 20 minutes. In some embodiments, the contact time can be between about 1 minute and 5 minutes. In some embodiments, the contact time can be between about 1 minute and about 3 minutes. In some embodiments, the contact time can be less than about 5 minutes. In some embodiments, the contact time can be about 2 minutes. In some embodiments, the contact time can be about 1 minutes.

The aqueous slurry of NCC can be passed over a fixed bed of zirconia catalyst (discussed in detail below) to allow the NCC particles to contact the surface active sites on the catalyst where it can be catalytically degraded from NCC into smaller oligomeric components. Under the supercritical conditions, the oligomeric components can hydrothermolytically react to produce phenolics, ketones, and the gaseous products such as carbon dioxide, methane, and ethylene. Exemplary phenolics can include, but not be limited to, phenol; 4-methyl phenol; 3,5-dimethyl phenol; 2-methyl phenol; 2,4-dimethyl phenol; 2,3-dimethyl phenol; 3-ethyl, 5-methyl phenol; and 4(2-propenyl) phenol. Exemplary ketones can include, but not be limited to, cyclopentanone; 3-methyl cyclopentanone; 3-hexanone; and 2-methyl cyclopentanone. In some embodiments, the reaction product mixture can include about 0.1 wt. % or less other phenolic and ketone isomers.

In some embodiments, the reaction products can be cooled and returned to ambient temperature for further processing. In some embodiments, a water insoluble product can be formed that has properties of a coal tar-like substance that contains a complex mixture of hydrocarbon molecules and oligomers (e.g., benzene and naphthalene). This water insoluble product can be removed and dissolved in solvents such as ether, acetone or cyclohexane and stored for further processing.

In some embodiments, the reaction product mixture can include at least about 0 to 80% by weight (wt. %) phenolics (as measured by GC-MS chromatographic peak area normalization method). In some embodiments, the reaction product mixture can include at least about 0 to 35 wt. % phenolics. In some embodiments, the reaction product mixture can include at least about 0 to 60 wt. % phenolics. In some embodiments, the reaction product mixture can include at least about 0 to 77 wt. % phenolics. In some embodiments, the reaction product mixture can include at least about 0, 10, 15, 20, 25, 30, 35, 40, 45, 50, 55, 60, 65, 70, 75, 80, 85, 90, or 95 wt. % phenolics. In some embodiments, the reaction product mixture can include a weight percentage of phenolics in a range between any of the foregoing multiples provided that the upper bound of the range is greater than the lower bound of the range.

In some embodiments, the reaction product mixture can include at least about 0 to 80 wt. % ketones (as measured by GC-MS chromatographic peak area normalization method). In some embodiments, the reaction product mixture can include at least about 0 to 25 wt. % ketones. In some embodiments, the reaction product mixture can include at least about 0 to 40 wt. % ketones. In some embodiments, the reaction product mixture can include at least about 0 to 70 wt. % ketones. In some embodiments, the reaction product mixture can include at least about 0, 10, 15, 20, 25, 30, 35, 40, 45, 50, 55, 60, 65, 70, 75, 80, 85, 90, or 95 wt. % ketones. In some embodiments, the reaction product mixture can include a weight percentage of ketones in a range between any of the foregoing multiples provided that the upper bound of the range is greater than the lower bound of the range.

In some embodiments, the reaction product mixture can include at least about 20 wt. % phenolics and at least about 10 wt. % ketones as a percentage of the total starting mass of the NCC.

In some embodiments, the proportion of phenolics amongst the total amount of phenolics to ketones in the reaction product mixture can be at least about 20, 25, 30, 35, 40, 45, 50, 55, 60, 65, 70, 75, 80, 85, or 90 wt. %. In some embodiments, the proportion of phenolics amongst the total amount of phenolics to ketones in the reaction product mixture can be in a range wherein any of the foregoing amounts can serve as the upper or lower bound of the range, provided that the upper bound is greater than the lower bound. In some embodiments, the proportion of phenolics amongst the total amount of phenolics to ketones in the reaction product mixture can be at least about 75 wt. %.

In some embodiments, the proportion of ketones amongst the total amount of phenolics to ketones in the reaction product mixture can be at least about 20, 25, 30, 35, 40, 45, 50, 55, 60, 65, 70, 75, 80, 85, or 90 wt. %. In some embodiments, the proportion of ketones amongst the total amount of phenolics to ketones in the reaction product mixture can be in a range wherein any of the foregoing amounts can serve as the upper or lower bound of the range, provided that the upper bound is greater than the lower bound. In some embodiments, the proportion of ketones amongst the total amount of phenolics to ketones in the reaction product mixture can be at least about 65 wt. %.

In some embodiments, the reaction product mixture can include at least about 10 wt. % cyclopentanone of the total phenolic and ketone content of the reaction product mixture. In some embodiments, the reaction product mixture can include at least about 8 wt. % phenol of the total phenolic and ketone content of the reaction product mixture. In some embodiments, 4-methyl phenol and phenol can account for at least 40 wt. % combined of the total phenolic content of the reaction product mixture. In some embodiments, 4-methyl phenol and phenol can account for at least 50 wt. % combined of the total phenolic content of the reaction product mixture.

In some embodiments, reaction products can include, but not be limited to, gaseous products such as carbon dioxide, methane, and ethylene gases. In some embodiments, the gaseous products can include at least about 50% by weight of the total starting mass of NCC. In some embodiments, the total amount of carbon dioxide gas can include at least about 48% by weight of the total starting mass of NCC. In some embodiments, the total amount of methane gas can include at least about 30% by weight of the total starting mass of NCC. In some embodiments, the total amount of ethylene gas can include at least about 22% by weight of the total starting mass of NCC.

Nanocrystalline Cellulose

Cellulosic source materials for use herein can include those that are renewable materials such as wood, cotton, straw, bark, algae, bacteria, etc. Cellulose is a polysaccharide known as poly 1,4-β-D-glucose. Using chemical or mechanical treatment, cellulose fibers with high molecular weight can be converted into cellulose nanofibers that have a crystalline structure. Cellulose fibrils with widths in the nanometer range are commonly known as nanocellulose.

Nanocellulose has been historically categorized based on source, mode of formation, and size into one of three categories: microfibrillated cellulose (MFC), nanocrystalline cellulose (NCC), or bacterial nanocellulose (BNC). NCC is ideally suited for use with some embodiments herein.

In some embodiments, NCC can be produced via acid hydrolysis followed by ultrasonic treatment. Suitable acids for use during the isolation of NCC from cellulose can include, but not be limited to, sulfuric acid, nitric acid, hydrochloric acid, phosphoric acid, maleic acid, and the like, or any combination thereof. In some embodiments, the acid used to produce NCC from cellulose is sulfuric acid. In some embodiments, the NCC used herein will include sulfur in small quantities, such as about 1.5 wt. % (or 13,000 ppm), as ionic sulfate groups that are found to solubilize and stabilize the NCC particles in aqueous solution. As a result of using sulfuric acid during formation of NCC, the reaction products can contain an organic portion having a small fraction of residual sulfur. In some embodiments, the reaction product mixture can include an organic portion having less than about 20 ppm sulfur. In some embodiments, the reaction product mixture can include an organic portion having less than about 15 ppm sulfur.

Commercially available NCC can be obtained from CelluForce, Montreal Quebec, Canada. NCC for use herein can include rod-shaped nanocrystals having widths from 5-70 nm and lengths between 100 to 1,000 nm. In some embodiments, NCC for use herein can include rod-shaped cellulose nanocrystals having widths of 5, 10, 20, 30, 40, 50, 60, or 70 nm. In some embodiments, NCC for use herein can include rod-shaped cellulose nanocrystals having lengths of 100, 200, 300, 400, 500, 600, 700, 800, 900, or 1000 nm. In some embodiments, the width and/or length of the NCC can be in a range between any of the foregoing multiples provided that the upper bound of the range is greater than the lower bound of the range.

As described herein, fluidic suspensions of NCC are well suited to enter micron-sized pores of a metal oxide catalyst bed, thus enabling its degradation into monosaccharides, the majority of which is glucose.

Other Reaction Mixture Components

In some embodiments, the reaction mixture can also include a material selected from the group consisting of lipids, proteins, and carbohydrates other than NCC. In some embodiments, the reaction mixture can also include one or more materials selected from both renewable carbon sources and non-renewable carbon sources. By way of example, renewable carbon sources can include, but are not limited to, plant-based, microorganism based, and/or animal based biomass. Renewable carbon sources can specifically include carboxylic acids, fatty acids, triglycerides, carbohydrates, biopolymers, and the like.

Renewable carbon sources can specifically include lipid feed stocks that can be derived from many different sources. In some embodiments, lipid feed stocks used in embodiments of the invention can include biological lipid feed stocks. Biological lipid feed stocks can include lipids (fats or oils) produced by any type of microorganism, fungus, plant or animal. In an embodiment, the biological lipid feed stocks used include triglycerides. Many different biological lipid feed stocks derived from plants can be used.

Plant-based feed stocks can include rapeseed oil, soybean oil (including degummed soybean oil), canola oil, cottonseed oil, grape seed oil, mustard seed oil, corn oil, linseed oil, safflower oil, sunflower oil, poppy-seed oil, pecan oil, walnut oil, oat oil, peanut oil, rice bran oil, *camellia* oil, castor oil, and olive oil, palm oil, coconut oil, rice oil, algae oil, seaweed oil, Chinese Tallow tree oil. Other plant-based biological lipid feed stocks can be obtained from argan, avocado, babassu palm, balanites, borneo tallow nut, brazil nut, calendula, camelina, caryocar, cashew nut, chinese vegetable tallow, cocoa, coffee, cohune palm, coriander, cucurbitaceae, *euphorbia*, hemp, illipe, jatropha, jojoba, kenaf, kusum, macadamia nuts, mango seed, noog *abyssinia*, nutmeg, opium poppy, *perilla*, pili nut, pumpkin seed, rice bran, sacha inche, seje, sesame, shea nut, teased, allanblackia, almond, chaulmoogra, *cuphea*, jatropa curgas, karanja seed, neem, *papaya*, tonka bean, tung, and ucuuba, cajuput, clausena anisata, davana, *galbanum* natural oleoresin, german chamomile, hexastylis, high-geraniol monarda, juniapa-hinojo sabalero, lupine, *melissa officinalis*, milfoil, ninde, patchouli, tarragon, and wormwood.

Many different feed stocks derived from animals can also be used. By way of example, animal-based biological lipid feed stocks can include choice white grease, lard (pork fat), tallow (beef fat), fish oil, and poultry fat.

Many different feed stocks derived from microorganisms (Eukaryotes, Eubacteria and Archaea) can also be used. By way of example, microbe-based lipid feed stocks can include the L-glycerol lipids of Archaea and algae and diatom oils. Many different lipid feed stocks derived from fungus (e.g. Yeasts) can also be used.

In some embodiments, feed stocks derived from both plant and animal sources can be used such as yellow grease, white grease, and brown grease. By way of example, yellow, white or brown grease can include frying oils from deep fryers and can thus include fats of both plant and animal origin. Lipid feed stocks can specifically include used cooking oil. Brown grease (also known as trap grease) can include fats extracted from waste water treatment and sewage systems and can thus include fats of both plant and animal origin. In some embodiments, lipid feed stocks used in embodiments of the invention can include non-biological lipid feed stocks. Lipid feed stocks of embodiments herein can include black oil.

In some embodiments, feed stocks can be derived from microorganisms such as bacteria, protozoa, algae (such as algae oil, whole algae biomass, algae paste, algae powder), and fungi. Lipid feed stocks of embodiments herein can also include soap stock and acidulated soap stock.

Lipid feed stocks used with embodiments of embodiments herein can specifically include low value feed stocks. Low value feed stocks, such as various types of animals fats and waste oils, generally have a relatively high concentration of free fatty acids. One method of assessing the concentration of free fatty acids is to determine the acid number (or acid value) of the feed stock. The acid number is the mass of potassium hydroxide (KOH) in milligrams that is required to neutralize one gram of the chemical substance being assessed. The precise acid number as measured can vary because of the heterogeneity of the lipid feed stock. However, as an example, a high value feed stock such as virgin soybean oil can have an acid number of about 0.35 whereas a lower value feed stock such as swine tallow can have an acid number of about 5. Yellow grease, a low value feed stock, can have an acid number of about 15 while acidulated soap stock, also a low value feed stock, can have an acid number of about 88.

In some embodiments, the feed stock used has an acid number of about 3 (mg KOH/g oil) or greater. In some embodiments, the feed stock used has an acid number of about 5 (mg KOH/g oil) or greater. In some embodiments, the feed stock used has an acid number of about 10 (mg KOH/g oil) or greater. In some embodiments, the feed stock used has an acid number of about 50 (mg KOH/g oil) or greater.

Carbohydrates used with embodiments herein can include, but are not limited to, monosaccharides, disaccharides, polysaccharides, and the like. Carbohydrates used with embodiments herein can specifically include cellulose and hemicellulose.

Other materials useful as feedstocks can include lignin, pectin, and the like.

Non-renewable carbon sources can include, but are not limited to, coal, carbonaceous gases, and petroleum, or fractions thereof.

Catalysts

Catalysts herein can include those exhibiting sufficient stability in the presence of supercritical water conditions (i.e., T≥350 degrees Celsius and P≥3,200 PSI). Catalysts herein can include metals, metal oxides, ceramics, and the like. Catalysts used with embodiments of the invention can include metal oxides with surfaces including Lewis acid sites, Bronsted base sites, and Bronsted acid sites. By definition, a Lewis acid is an electron pair acceptor. A Bronsted base is a proton acceptor and a Bronsted acid is a proton donor.

Catalysts of embodiments herein can specifically include zirconia, titania, hafnia, yttria, tungsten (VI) oxide, manganese oxide, nickel oxide, nickel, copper oxide, niobium oxide, cobalt oxide, carbon, carbon/nickel, carbon/platinum. In some embodiments catalysts can include alumina, iron oxide, metal salts, insoluble metal salts, metal oxides, metal hydroxides, metal alloys, metal complexes, and metal ion complexes. Metals of these can include alkali metals, alkaline earth metals, transition metals and poor metals. In some embodiments, the metal can include one or more of group IA, IIA, IIB, IVB, VB, VIB, VIIB, VIIIB, IB, IIB, IIIA, IVA metals. In some embodiments, the catalyst can include one or more of $CuO$, $KH_2PO_4$, $Nb_2O_5$, $Y_2O_3$, $ZnO$, $MgCO_3$, $K_2CO_3$, $Fe_2O_3$, and $CoO_2$. In some embodiments, the catalyst can consist essentially of one or more of any of the materials described herein.

In some embodiments, the catalyst can be, or include, a metal oxide that is stable at temperatures above 350 degrees Celsius in the presence of supercritical water. In some embodiments, the catalyst can be, or include, a metal oxide that is stable at temperatures above 400 degrees Celsius in the presence of supercritical water. In some embodiments, the catalyst can be, or include, a metal oxide that is stable at temperatures above 450 degrees Celsius in the presence of supercritical water. In some embodiments, the catalyst can be, or include, a metal oxide that is stable at temperatures above 500 degrees Celsius in the presence of supercritical water. In some embodiments, the catalyst can be, or include, a metal oxide that is stable at temperatures above 550 degrees Celsius in the presence of supercritical water. In some embodiments, the catalyst can consist essentially of any of the foregoing.

Catalysts of embodiments herein can also include silica clad with any of the foregoing catalyst materials, such as a metal oxide selected from the group consisting of zirconia, titania, hafnia, yttria, tungsten (VI) oxide, manganese oxide, nickel oxide, nickel, copper oxide, niobium oxide, cobalt oxide, carbon carbon/nickel, carbon/platinum.

In some embodiments, the catalyst can be of a single metal oxide type. By way of example, in some embodiments, the catalyst is substantially pure zirconia. By way of example, in some embodiments, the catalyst is substantially pure titania. By way of example, in some embodiments, the catalyst is substantially pure hafnia. By way of example, in some embodiments, the catalyst is substantially pure yttria. By way of example, in some embodiments, the catalyst is substantially pure tungsten (VI) oxide. By way of example, in some embodiments, the catalyst is substantially pure manganese oxide. By way of example, in some embodiments, the catalyst is substantially pure nickel oxide.

Catalysts of embodiments herein can also include mixtures of materials, such as mixtures of materials including zirconia, titania, hafnia, yttria, tungsten (VI) oxide, manganese oxide, nickel oxide, nickel, carbon, carbon/nickel, and carbon/platinum.

In some embodiments, the catalyst can consist essentially of zirconia. Zirconia catalyst particles for use herein can be thermally and chemically stable under supercritical water conditions (i.e., T≥350 degrees Celsius and P≥3,200 PSI). Exemplary zirconia catalysts are commercially available from ZirChrom Separations of Anoka, Minn. Suitable zirconia catalyst particles for use herein can maintain a well-defined pore structure and are stable under both high pressure (6,000 PSI) and high temperature (600 degrees Celsius) conditions. In some embodiments, the zirconia catalyst can be porous and spherical, with an average diameter of 25 microns. Zirconia is also well-suited for the embodiments herein due to its high chemical stability over the entire pH range, from pH of 1 to a pH of 14.

Catalysts of embodiments herein can include metal oxide particles clad with carbon. Carbon clad metal oxide particles can be made using various techniques such as the procedures described in U.S. Pat. Nos. 5,108,597; 5,254,262; 5,346,619; 5,271,833; and 5,182,016, the contents of which are herein incorporated by reference. Carbon cladding on metal oxide particles can render the surface of the particles more hydrophobic.

Catalysts of embodiments herein can be made in various ways. As one example, a colloidal dispersion of zirconium dioxide can be spray dried to produce aggregated zirconium dioxide particles. Colloidal dispersions of zirconium dioxide are commercially available from Nyacol Nano Technologies, Inc., Ashland, Mass. The average diameter of particles produced using a spray drying technique can be varied by changing the spray drying conditions. Examples of spray drying techniques are described in U.S. Pat. No. 4,138,336 and U.S. Pat. No. 5,108,597, the contents of both of which are herein incorporated by reference. It will be appreciated that other methods can also be used to create metal oxide particles. One example is an oil emulsion technique as described in Robichaud et al., Technical Note, "An Improved Oil Emulsion Synthesis Method for Large, Porous Zirconia Particles for Packed- or Fluidized-Bed Protein Chromatography," Sep. Sci. Technol. 32, 2547-59 (1997). A second example is the formation of metal oxide particles by polymer induced colloidal aggregation as described in M. J. Annen, R. Kizhappali, P. W. Carr, and A. McCormick, "Development of Porous Zirconia Spheres by Polymerization-Induced Colloid Aggregation-Effect of Polymerization Rate," J. Mater. Sci. 29, 6123-30 (1994). A polymer induced colloidal aggregation technique is also described in U.S. Pat. No. 5,540,834, the contents of which are herein incorporated by reference.

Metal oxide catalysts used in embodiments of the invention can be sintered by heating them in a furnace or other heating device at a relatively high temperature. In some embodiments, the metal oxide is sintered at a temperature of about 160° C. or greater. In some embodiments, the metal oxide is sintered at a temperature of about 400° C. or greater. In some embodiments, the metal oxide is sintered at a temperature of about 600° C. or greater. Sintering can be done for various amounts of time depending on the desired effect. Sintering can make metal oxide catalysts more durable. In some embodiments, the metal oxide is sintered for more than about 30 minutes. In some embodiments, the metal oxide is sintered for more than about 3 hours. However, sintering also reduces the surface area. In some embodiments, the metal oxide is sintered for less than about 1 week.

In some embodiments, the catalyst is in the form of particles. Particles within a desired size range can be specifically selected for use as a catalyst. For example, particles can be sorted by size using techniques such as air classification, elutriation, settling fractionation, or mechanical screening. In some embodiments, the size of the particles is greater than about 0.2 μm. In some embodiments, the size range selected is from about 50 nm to about 50 mm. In some embodiments, the size range selected is from about 0.2 μm to about 10 mm. In some embodiments, the size range selected is from about 0.2 μm to about 5 mm. In some embodiments, the size range selected is from about 0.2 μm to about 1 mm. In some embodiments, the size range selected is from about 1 μm to about 100 μm. In some embodiments, the size range selected is from about 5 μm to about 15 μm. In some embodiments, the average size selected is about 10 μm. In some embodiments, the average size selected is about 5 μm.

In some embodiments, the catalyst can be a particulate in the nanometer size range. In some embodiments, the catalyst can be from about 0.1 nm to about 500 nm. In some embodiments, the catalyst can be from about 1.0 nm to about 300 nm. In some embodiments, the catalyst can be from about 5.0 nm to about 200 nm. In some embodiments, the catalyst can be used in the form of a colloid.

In some embodiments, catalyst particles used with embodiments of the invention are porous. By way of example, in some embodiments the particles can have an average pore size of about 30 angstroms to about 2000 angstroms. However, in other embodiments, catalyst particles used are non-porous.

The physical properties of a porous catalyst can be quantitatively described in various ways such as by surface area, pore volume, porosity, and pore diameter. In some embodiments, catalysts of embodiments herein can have a surface area of between about 1 and about 1000 m$^2$/gram. In some embodiments, catalysts of embodiments herein can have a surface area of between about 1 and about 400 m$^2$/gram. In some embodiments, the catalyst of embodiments herein can have a surface area much higher than 400 m$^2$/gram.

In some embodiments, catalysts of embodiments herein can have a surface area of between about 1 and about 200 m$^2$/gram. Pore volume refers to the proportion of the total volume taken up by pores in a material per weight amount of the material. In some embodiments, catalysts of embodiments herein can have a pore volume of between about 0.01 mL/g and about 2 mL/g. Porosity refers to the proportion within a total volume that is taken up by pores. As such, if the total volume of a particle is 1 cm$^3$ and it has a porosity of 0.5, then the volume taken up by pores within the total volume is 0.5 cm$^3$. In some embodiments, catalysts of embodiments herein can have a porosity of between about 0 and about 0.8. In some embodiments, catalysts of embodiments herein can have a porosity of between about 0.3 and 0.6.

Catalyst particles used with embodiments of the invention can have various shapes. By way of example, in some embodiments the particle can be in the form of spherules. In other embodiments, the particle can be a monolith. In some embodiments, the particle can have an irregular shape.

The Lewis acid sites on catalysts of embodiments herein can interact with Lewis basic compounds. Thus, in some embodiments, Lewis basic compounds can be bonded to the surface of catalysts. However, in other embodiments, the catalysts used with embodiments herein are unmodified and have no Lewis basic compounds bonded thereto. A Lewis base is an electron pair donor. Lewis basic compounds of embodiments herein can include anions formed from the dissociation of acids such as hydrobromic acid, hydrochloric acid, hydroiodic acid, nitric acid, sulfuric acid, perchloric acid, boric acid, chloric acid, phosphoric acid, pyrophosphoric acid, chromic acid, permanganic acid, phytic acid and ethylenediamine tetramethyl phosphonic acid (EDTPA), and the like. Lewis basic compounds of embodiments herein can also include hydroxide ion as formed from the dissociation of bases such as sodium hydroxide, potassium hydroxide, lithium hydroxide and the like.

The anion of an acid can be bonded to a metal oxide of embodiments herein by refluxing the metal oxide in an acid solution. By way of example, metal oxide particles can be refluxed in a solution of sulfuric acid. Alternatively, the anion formed from dissociation of a base, such as the hydroxide ion formed from dissociation of sodium hydroxide, can be bonded to a metal oxide by refluxing in a base solution. By way of example, metal oxide particles can be refluxed in a solution of sodium hydroxide. The base or acid modification can be achieved under exposure to the acid or base in either batch or continuous flow conditions when disposed in a reactor housing at elevated temperature and pressure to speed up the adsorption/modification process. In some embodiments, fluoride ion, such as formed by the dissociation of sodium fluoride, can be bonded to the particles.

In some embodiments, catalyst particles can be packed into a housing, such as a column. Disposing catalyst particles in a housing is one approach to facilitating continuous flow processes. Many different techniques can be used for packing the catalyst particles into a housing. The specific technique used may depend on factors such as the average particle size, the type of housing used, etc. Generally speaking, particles with an average size of about 1-20 microns can be packed under pressure and particles with an average size larger than 20 microns can be packed by dry-packing/tapping methods or by low pressure slurry packing. In some embodiments, the catalyst particles of embodiments herein can be impregnated into a membrane, such as a PTFE membrane.

However, in some embodiments, catalysts used with embodiments of the invention are not in particulate form. For example, a layer of a metal oxide can be disposed on a substrate in order to form a catalyst used with embodiments of the invention. The substrate can be a surface that is configured to contact the feedstocks during processing. In one approach, a catalyst can be disposed as a layer over a surface of a reactor that contacts the feedstocks. Alternatively, the catalyst can be embedded as a particulate in the surface of an element that is configured to contact the feedstocks during processing.

Conversion of NCC to Phenolics and Ketones

Figure 3:
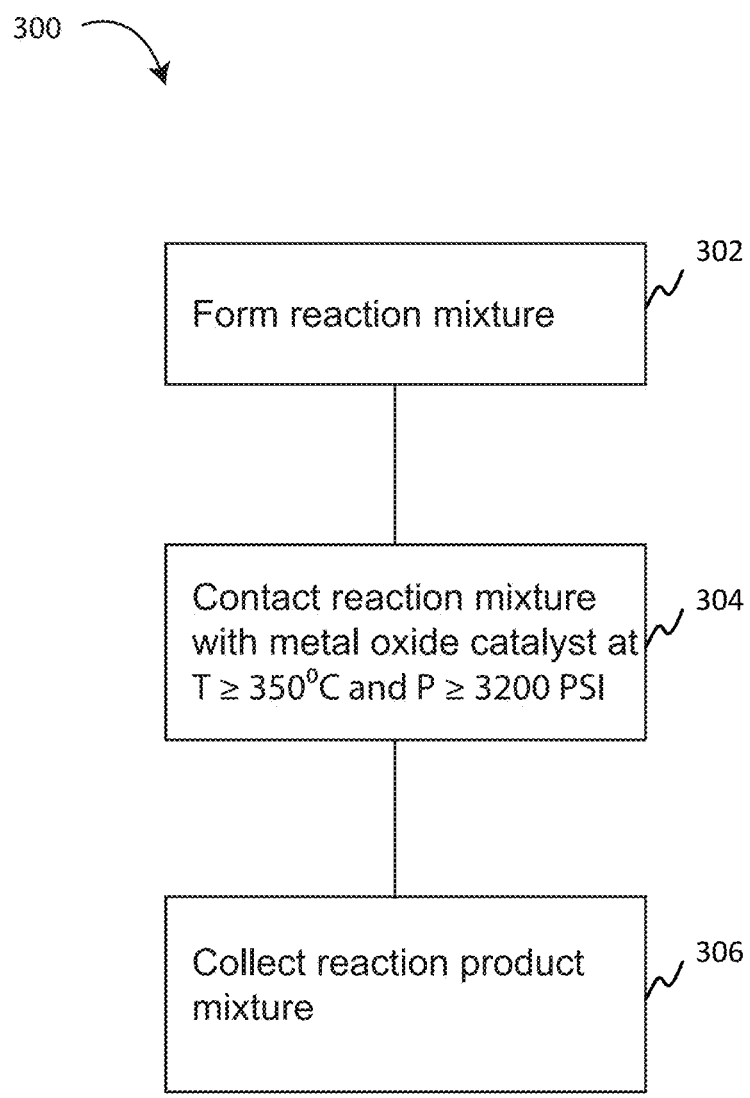
FIG. 3 is a flow diagram of a method of converting NCC to phenolics and ketones in accordance with the embodiments herein.

Referring now to FIG. 3, a flow diagram is shown of a method 300 for producing phenolics and ketones in accordance with the embodiments herein. The method begins by forming a reaction mixture of NCC and water at step 302. The reaction mixture is then contacted with a metal oxide catalyst at a temperature of greater than or equal to 350 degrees Celsius and a pressure of greater than or equal to 3200 PSI at step 304 to form a reaction product mixture. The reaction product mixture can then be collected in step 306. In some embodiments, the method can include contacting the reaction mixture at a temperature greater than 100 degrees Celsius in a solubilization chamber prior to contacting the reaction mixture with the metal oxide catalyst. In some embodiments, the method can be performed as a continuous flow process. In some embodiments, the method can include pre-heating the reaction mixture prior to contacting it with a metal oxide catalyst. In some embodiments, the reaction product mixture can be cooled before collection.

Aspects may be better understood with reference to the following examples. These examples are intended to be representative of specific embodiments, but are not intended as limiting the overall scope of embodiments herein.

EXAMPLES

Example 1: Formation of Zirconia Reaction Columns

Porous zirconia catalyst having 25 micron sized pores and well-defined particle size and surface area was obtained in sufficient quantity from ZirChrom® Separations Inc. (Anoka, Minn.). Zirconia particles were packed at ZirChrom® Separations (Anoka, Minn.) into a reactor column using a downward slurried high-pressure packing station (Alltech Associates, Deerfield, Ill.) using a high-pressure packing pump from Haskel (Burbank, Calif.). The particles were packed into all stainless steel high performance liquid chromatographic (HPLC) column hardware obtained from Isolation Technologies (Hopedale, Mass.). The reactor column was outfitted with 10-micron inlet and 2-micron outlet stainless steel frits.

In specific, the reactor column had dimensions of 1.0 cm i.d.×15 cm length. A particle slurry was first formed by adding a modified zirconium oxide in HPLC-grade methanol. The slurry was then packed into the stainless steel reactor column at 7,000 PSI using methanol as the pusher solvent. The reactor column was allowed to pack and compress for 30 minutes under constant pressure. The high pressure packing pump was shut off after 30 minutes and the reactor column was allowed to slowly bleed off pressure while remaining attached to the packing apparatus. When the pressure was fully released, the reactor column was disconnected from the apparatus and the frit and end fitting was attached to the inlet to complete construction of the reactor column.

Example 2: Continuous Phenolic and Ketone Production System Design

Figure 4:
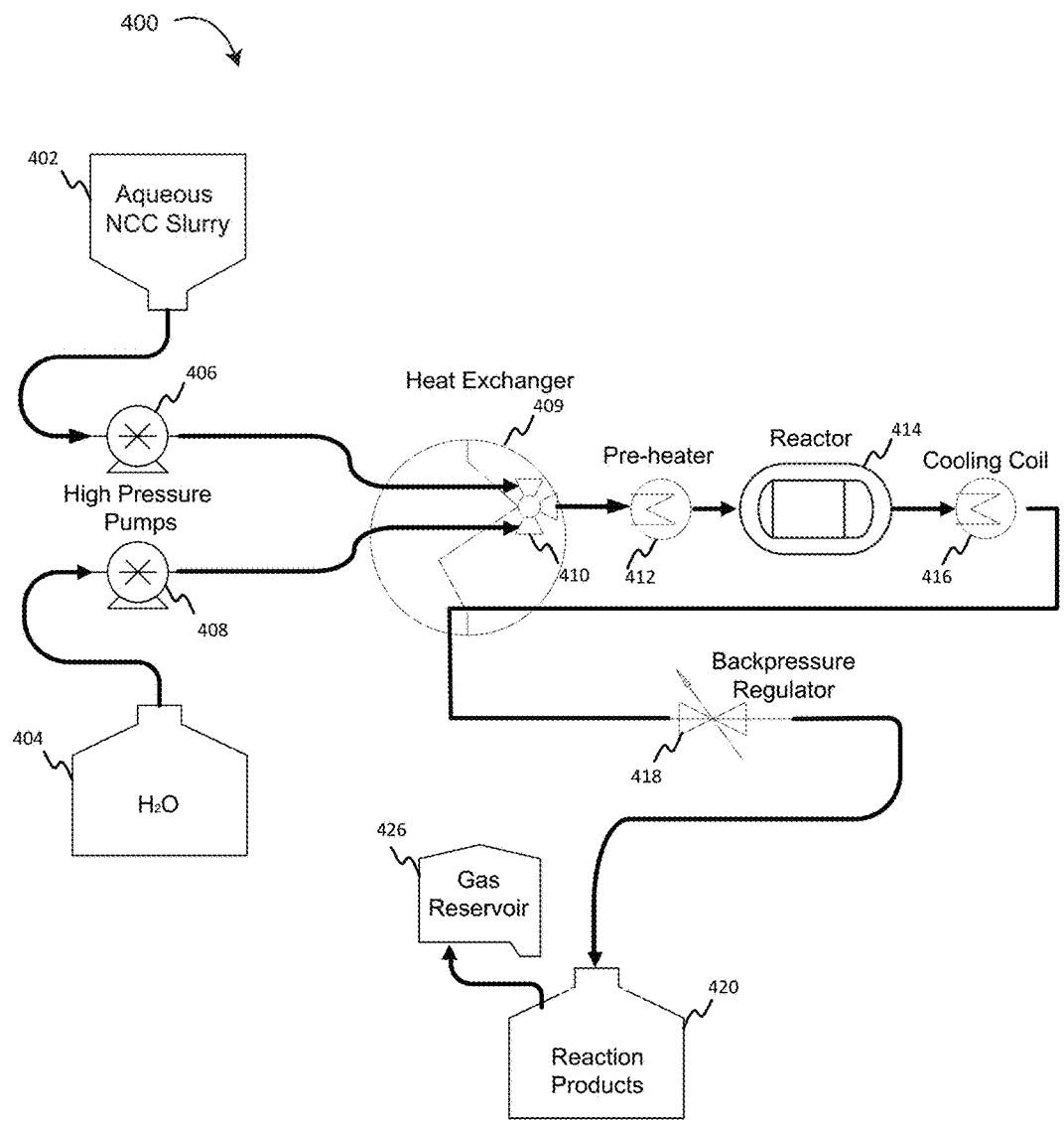
FIG. 4 is a schematic diagram of a reactor system in accordance with the embodiments herein.

A schematic of the continuous production process reactor system 300 used in the Examples 3 and 4 herein is shown in FIG. 4. An aqueous slurry of NCC was held in NCC suspension reservoir 402 and heated water was held in water suspension reservoir 404. Two high pressure Waters 590 HPLC pumps 406 and 408 were obtained from Waters Corporation (Milford, Mass.). Water pumps 406 and 408 pulled from heated water reservoir 404 and a NCC suspension reservoir 402, both of which were continuously sparged with nitrogen to minimize the effect of dissolved oxygen on the system.

The heated water and NCC slurry were pumped into a custom designed heat exchanger 409 that consisted of two silver-soldered ⅛th in. o.d. stainless steel tubes (Alltech Associates, Deerfield, Ill.). The heat from the hot reaction product effluent from the reactor was exchanged with the incoming reactant streams. After passing through the heat exchanger 309, the two reactant streams were combined using a "T" 410 and then passed through an electrically driven preheater 412 capable of bringing the mixture to the desired set point temperature before entering into the fixed bed catalytic reactor vessel 414. The temperature control was achieved using EZ-Zone PM Watlow (St. Louis, Mo.) temperature controllers.

Reactor vessel 414 consisted of a stainless steel HPLC tubing wound about a grooved aluminum cylindrical block, with an 800 watt Watlow heater in the center of the cylinder. Reactor vessel 414 was packed with a porous zirconia catalyst having 25 micron sized pores and well-defined particle size and surface area (ZirChrom® Separations Inc., Anoka, Minn.). After passing through the reactor vessel 414, the reaction products were passed through cooling coil 416 to bring the reaction products back to room temperature.

The backpressure of the system was maintained using a backpressure regulator 418 obtained from Tescom (Elk River, Minn.) The backpressure regulator 418 was placed in line at the end of the tubing after the reaction tubing was cooled to room temperature at cooling coil 416. The non-gaseous reaction products were received in reaction product reservoir 420. The gaseous reaction products were collected in gas reservoir 426.

Example 3: Continuous Production of Phenolics and Ketones at Elevated Temperature and Pressure The continuous production of phenolics and ketones from a slurry of NCC in supercritical water was investigated at 450, 500, 525, and 550° C., and a pressure of ≥3200 PSI. As discussed previously, about 50% by weight of the total starting mass of NCC is converted to gaseous products (data not shown) during the continuous production processes described herein. The remaining 50% by weight of the total starting mass of NCC is converted into a non-gaseous product mixture composition, including phenolics and ketones. The non-gaseous products were extracted with ether, separated, and dried in sodium sulfate prior to quantitative analysis by GC-MS. The main non-gaseous products were ketones, including cyclopentanone, and phenolics, including phenol.

Figure 5:
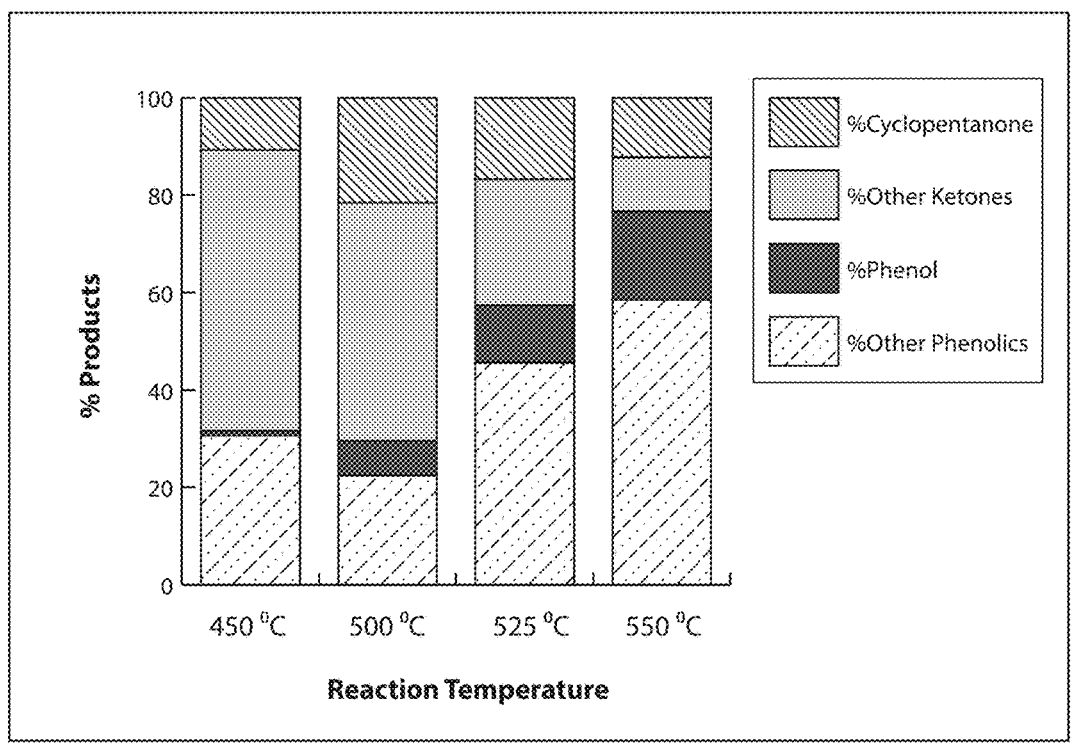
FIG. 5 is a graph of phenolic and ketone reaction product distribution at various temperatures in accordance with various embodiments herein.

Referring now to Table 1 and FIG. 5, shown is the weight percentage distribution of non-gaseous products as a function of increased reaction temperature. At 450° C., the production of ketones predominates the reaction product mixture, with close to 70% weight percent of the total mass of reaction products being ketone. As the temperature increased to 550° C., the production of phenolics predominated in the reaction product mixture, with close to 77% weight percent of the total mass of reaction products as phenolics. In addition, the total weight percent of cyclopentanone and phenol, as compared to the total mass percent of ketones or phenolics, respectively, increased as reaction temperature increased.

TABLE 1

Distribution of Non-gaseous Phenolic and Ketone Reaction Products of Nanocrystalline Cellulose Degradation at Supercritical Water Conditions

| Temp. ° C. | Other Phenolics (wt. %) | Phenol (wt. %) | Other Ketones (wt. %) | Cyclopentanone (wt. %) |
|---|---|---|---|---|
| 450 | 30.6 | 1.1 | 57.5 | 10.8 |
| 500 | 22.4 | 7.1 | 48.9 | 21.6 |
| 525 | 45.6 | 11.8 | 25.8 | 16.8 |
| 550 | 58.5 | 18.1 | 11.1 | 12.3 |

Example 4: Production of Primary, Secondary, Ternary, Reaction Products

Figure 6:
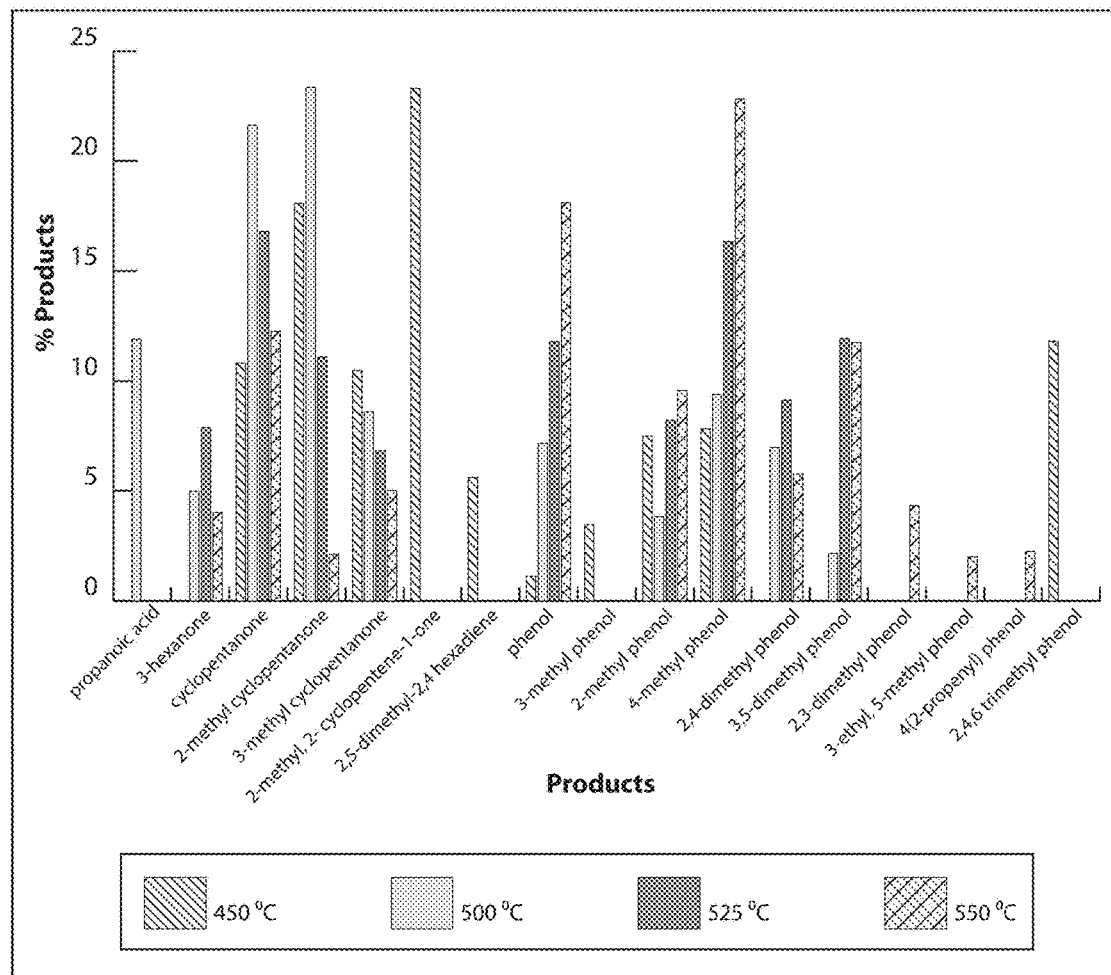
FIG. 6 is a graph of specific phenolic and ketone reaction product distributions at various temperatures in accordance with various embodiments herein.

The continuous production of individual phenolics and ketones from a slurry of NCC in supercritical water was investigated at 450, 500, 525, and 550° C., and a pressure of ≥3200 PSI. FIG. 6 and Table 2 shows the distribution of individual phenolics and ketones found to predominate the reaction product mixture as measured by GC-MS chromatographic peak area normalization method. Phenolics isolated during the process include phenol; 4-methyl phenol; 3,5-dimethyl phenol; 2-methyl phenol; 2,4-dimethyl phenol; 2,3-dimethyl phenol; 3-ethyl,5-methyl phenol; and 4(2-propenyl) phenol. Ketones isolated during the process include cyclopentanone; 3-methyl cyclopentanone; 3-hexanone; and 2-methyl cyclopentanone.

TABLE 2

Distribution of Primary, Secondary, and Ternary Reaction Products of Nanocrystalline Cellulose Degradation at Supercritical Water Conditions

| Reaction Product | Temperature (° C.) | | | |
|---|---|---|---|---|
|  | 450 | 500 | 525 | 550 |
| propanoic acid | 0 | 11.9122 | 0 | 0 |
| 3-hexanone | 0 | 4.9771 | 7.8684 | 4.0148 |
| cyclopentanone | 10.8235 | 21.6218 | 16.7915 | 12.2551 |
| 2-methyl cyclopentanone | 18.0812 | 23.3728 | 11.1045 | 2.1186 |
| 3-methyl cyclopentanone | 10.4931 | 8.6146 | 6.8280 | 5.0116 |
| 2-methyl, 2-cyclopentene-1-one | 23.3176 | 0 | 0 | 0 |
| 2,5 dimethyl-2,4 hexadiene | 5.6027 | 0 | 0 | 0 |
| phenol | 1.1205 | 7.1496 | 11.7855 | 18.0999 |
| 3-methyl phenol | 3.4613 | 0 | 0 | 0 |
| 2-methyl phenol | 7.4775 | 3.8257 | 8.2044 | 9.5812 |
| 4-methyl phenol | 7.8141 | 9.4098 | 16.3432 | 22.8411 |
| 2,4-dimethyl phenol | 0 | 6.9690 | 9.1388 | 5.7561 |
| 3,5-dimethyl phenol | 0 | 2.1474 | 11.9356 | 11.7575 |
| 2,3-dimethyl phenol | 0 | 0 | 0 | 4.3211 |
| 3-ethyl, 5-methyl phenol | 0 | 0 | 0 | 2.0037 |
| 4(2-propenyl) phenol | 0 | 0 | 0 | 2.2394 |
| 2,4,6 trimethyl phenol | 11.8084 | 11.9122 | 0 | 0 |

The embodiments described herein are not intended to be exhaustive or to limit the invention to the precise forms disclosed in the following detailed description. Rather, the embodiments are chosen and described so that others skilled in the art can appreciate and understand the principles and practices.

All publications and patents mentioned herein are hereby incorporated by reference. The publications and patents disclosed herein are provided solely for their disclosure. Nothing herein is to be construed as an admission that the inventors are not entitled to antedate any publication and/or patent, including any publication and/or patent cited herein.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration to. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

Aspects have been described with reference to various specific and preferred embodiments and techniques. However, it should be understood that many variations and modifications may be made while remaining within the spirit and scope herein.

The invention claimed is:

1. A method of producing phenolics and ketones comprising:
    forming a reaction mixture comprising
    nanocrystalline cellulose (NCC); and
    water; and
    contacting the reaction mixture with a metal oxide catalyst at a temperature of 350 degrees Celsius or higher and a pressure of at least about 3200 psi to form a reaction product mixture, the reaction product mixture comprising at least about 20 wt. % phenolics and at least about 10 wt. % ketones as a percentage of the total mass of nanocrystalline cellulose (NCC).

2. The method of claim 1, the reaction mixture further comprising a material selected from the group consisting of lipids, proteins, and carbohydrates other than NCC.

3. The method of claim 1, wherein the temperature and pressure conditions are supercritical for water.

4. The method of claim 1, the nanocrystalline cellulose comprising rod-shaped cellulose crystals with widths from 5 to 70 nm and lengths from 100 to 1,000 nm.

5. The method of claim 1, wherein the temperature is greater than 374 degrees Celsius.

6. The method of claim 1, wherein the temperature is between about 374 and 600 degrees Celsius.

7. The method of claim 1, wherein the temperature is between about 500 and 600 degrees Celsius.

8. The method of claim 1, wherein the proportion of phenolics amongst the total amount of phenolics and ketones in the reaction product mixture is at least about 55 wt. %.

9. The method of claim 1, wherein the proportion of phenolics amongst the total amount of phenolics and ketones in the reaction product mixture is at least about 75 wt. %.

10. The method of claim 1, wherein the temperature is between about 374 and 525 degrees Celsius.

11. The method of claim 1, wherein the proportion of ketones amongst the total amount of phenolics and ketones in the reaction product mixture is at least about 60 wt. %.

12. The method of claim 1, wherein the proportion of ketones amongst the total amount of phenolics and ketones in the reaction product mixture is at least about 65 wt. %.

13. The method of claim 1, the reaction product mixture comprising at least about 10 wt. % cyclopentanone of the total phenolic and ketone content of the reaction product mixture.

14. The method of claim 1, the reaction product mixture comprising at least about 8 wt. % phenol of the total phenolic and ketone content of the reaction product mixture.

15. The method of claim 1, wherein 4-methyl phenol and phenol account for at least 40 wt. % combined of the total phenolic content of the reaction product mixture.

16. The method of claim 1, wherein 4-methyl phenol and phenol account for at least 50 wt. % combined of the total phenolic content of the reaction product mixture.

17. The method of claim 1, wherein the product mixture includes a liquid portion and at least about 80 wt. % of the liquid portion is phenolics and ketones.

18. The method of claim 1, wherein the product mixture includes a liquid portion and at least about 95 wt. % of the liquid portion is phenolics and ketones.

19. The method of claim 1, wherein the reaction product mixture includes an organic portion having less than about 20 ppm sulfur.

20. The method of claim 1, wherein the reaction product mixture includes an organic portion having less than about 15 ppm sulfur.

21. The method of claim 1, wherein the contact time is less than about five minutes.

22. The method of claim 1, wherein the contact time is about two minutes.

23. The method of claim 1, further comprising contacting the NCC with water at a temperature of greater than 100 degrees Celsius in a solubilization chamber to form the reaction mixture prior to contacting the reaction mixture with the metal oxide catalyst.

24. The method of claim 1, the metal oxide catalyst selected from the group consisting of zirconia, titania, and hafnia.

25. The method of claim 1, the metal oxide catalyst comprising spherical porous zirconia having an average diameter of 25 microns.

26. The method of claim 1, wherein the method is performed as a continuous flow process.

27. A system for producing a reaction product mixture including phenolics and ketones comprising:
    a feedstock tank comprising a nanocrystalline cellulose (NCC) feedstock;
    a water supply line;
    a reactor vessel in direct or indirect fluid communication with the feedstock tank and the water supply line;
    a plurality of metal oxide catalyst particles disposed within the reactor vessel;
    a heating element; and
    a back pressure regulator in fluid communication with the reactor vessel.

28. The system of claim 27, the heating element configured to maintain the temperature within the reactor vessel between about 374 and 600 degrees Celsius.

29. The system of claim 27, further comprising a high pressure pump in fluid communication with the feedstock tank.

30. The system of claim 27, further comprising a solubilization chamber in fluid communication between the feedstock tank and the reactor vessel.

* * * * *